(12) United States Patent
Lange et al.

(10) Patent No.: US 7,585,494 B2
(45) Date of Patent: Sep. 8, 2009

(54) FORMULATIONS USED FOR THE TREATMENT OF SUBSTRATE SURFACES

(75) Inventors: Horst Lange, Bochum (DE); Christopher Roos, Cologne (DE); Roland Wagner, Bonn (DE); Martin Kropfgans, Odenthal (DE); Andrew Russell Graydon, Tyne and Wear (GB); Richard Timothy Hartshorn, Cincinnati, OH (US); Jean-Pol Boutique, Gembloux (BE); Patrick Firmin August Delplanque, Laarne (BE); James Pyott Johnston, Merchtem (BE)

(73) Assignee: Momentive Performance Materials GmbH, Leverkusen (DE)

( * ) Notice: Subject to any disclaimer, the term of this patent is extended or adjusted under 35 U.S.C. 154(b) by 507 days.

(21) Appl. No.: 10/533,746

(22) PCT Filed: Oct. 31, 2003

(86) PCT No.: PCT/EP03/50772

§ 371 (c)(1), (2), (4) Date: Mar. 20, 2006

(87) PCT Pub. No.: WO2004/046452

PCT Pub. Date: Jun. 3, 2004

(65) Prior Publication Data

US 2006/0163524 A1    Jul. 27, 2006

(30) Foreign Application Priority Data

Nov. 4, 2002   (DE)   ................. 102 51 525

(51) Int. Cl.
*A61Q 5/02*    (2006.01)

(52) U.S. Cl. .................. 424/70.122; 510/329; 510/535; 510/330; 510/466; 252/8.63; 442/102; 442/157

(58) Field of Classification Search ............ 424/70.122; 510/329, 330, 466, 535; 252/8.63; 442/102, 442/157; 528/38

See application file for complete search history.

(56) References Cited

U.S. PATENT DOCUMENTS

| | | |
|---|---|---|
| 4,620,878 A | 11/1986 | Gee |
| 5,403,886 A | 4/1995 | Chrobaczek et al. |
| 5,707,434 A | 1/1998 | Halloran et al. |
| 5,707,435 A | 1/1998 | Halloran |
| 6,080,686 A | 6/2000 | Floyd |
| 7,217,777 B2 * | 5/2007 | Lange et al. ................ 528/28 |
| 7,390,479 B2 * | 6/2008 | Sockel et al. ............ 424/70.12 |

FOREIGN PATENT DOCUMENTS

WO    02/10257    *   2/2002

OTHER PUBLICATIONS

English abstract WO 02/10257, Feb. 2002.*

* cited by examiner

*Primary Examiner*—Margaret G Moore
(74) *Attorney, Agent, or Firm*—Rankin, Hill & Clark LLP

(57) ABSTRACT

The invention relates to formulations containing at least one nitrogen-free polysiloxane compound, at least one polyamino polysiloxane and/or polyammonium polysiloxane compound, and/or at least one amino polysiloxane and/or ammonium polysiloxane compound, and an optional silicone-free cationic surfactant, a coacervate phase-forming agent, and carrier substances. Also disclosed are a method for the production of the inventive formulations and the use thereof for treating natural and synthetic fibrous materials.

20 Claims, No Drawings

FORMULATIONS USED FOR THE TREATMENT OF SUBSTRATE SURFACES

The invention relates to formulations based on polysiloxane, to processes for their preparation and to their use, especially for the treatment of textiles and other natural and synthetic fiberlike materials.

Amino-containing polysiloxanes are known as textile softeners (EP 441530). The introduction of amino structures modified by ethylene oxide/propylene oxide units as side chains brings about an improvement in the effect (U.S. Pat. No. 5,591,880, U.S. Pat. No. 5,650,529). In this context, the alkylene oxide units allow the controlled adjustment of the hydrophilic-hydrophobic balance.

It has likewise been proposed to react $\alpha,\omega$-epoxy-modified siloxanes with $\alpha,\omega$-amino-functionalized alkylene oxides, and to use these products as hydrophilic softeners (U.S. Pat. No. 5,807,956, U.S. Pat. No. 5,981,681).

To improve the substantivity, experiments on the introduction of quaternary ammonium groups into alkylene oxide-modified siloxanes have been undertaken.

Branched alkylene oxide-modified polysiloxane quats ("polysiloxane quats"=quaternary ammonium-containing polysiloxanes) have been synthesized by condensation from $\alpha,\omega$-OH-terminated polysiloxanes and trialkoxysilanes. The quaternary ammonium structure is introduced via the silane, and the quaternary nitrogen atom is substituted by alkylene oxide units (U.S. Pat. No. 5,602,224).

Strictly comb-type alkylene oxide-modified polysiloxane quats have likewise been described. The hydroxyl groups of polyethersiloxanes substituted in a comblike manner are converted using epichlorohydrin (U.S. Pat. No. 5,098,979) or chloroacetic acid (U.S. Pat. No. 5,153,294, U.S. Pat. No. 5,166,297) to the corresponding chlorine derivatives. Subsequently, quaternization is effected with tertiary amines.

U.S. Pat. No. 6,242,554 describes $\alpha,\omega$-difunctional siloxane derivatives, each of which have a separate quaternary ammonium and alkylene oxide unit. These materials feature improved compatibility with polar environments.

The reaction of $\alpha,\omega$-diepoxides with tertiary amines in the presence of acids affords $\alpha,\omega$-diquaternary siloxanes which can be used for haircare purposes (DE-A-37 19 086). In addition to tetraalkyl-substituted quaternary ammonium structures, aromatic imidazolium derivatives are also claimed.

A reduction in the washout from hair can be achieved when the $\alpha,\omega$-diepoxides are reacted with tertiary diamines in the presence of acids to give long-chain polyquaternary polysiloxanes (EP-A-282 720). Aromatic quaternary ammonium structures are not disclosed.

Such polyquaternary imidazolium derivatives are considered in U.S. Pat. No. 6,240,929. These cationic compounds are said to have a further increased compatibility toward the anionic surfactants present in cosmetic formulations. However, the washout resistance from hair relates to the brief attack of principally water and very mild surfactants which do not irritate the skin, while wash-resistant hydrophilic softeners for textiles have to resist the attack of concentrated surfactant solutions with high grease and soil dissolution capacity. An additional complicating factor is that modern detergents comprise highly alkaline complexing agents, oxidative bleaches and complex enzyme systems, and the fibers are often exposed to their action at elevated temperatures over a period of hours.

Highly charged, very hydrophilic synthetic polycationic compounds are likewise capable of improving the compatibility with anionic surfactant systems (U.S. Pat. No. 6,211, 139) or of associating with fibers in the presence of solutions of anionic surfactants (WO 99/14300). The latter document also describes polyimidazolium derivatives inter alia. Mixtures of cationic polysaccharide derivatives with polysiloxanes have likewise been investigated (J. V. Gruber et al., Colloids and Surfaces B: Biointerfaces 19 (2000) 127-135).

It is also known that hydrocarbon-based quats which are used extensively, for example, in fabric softeners can be combined with polysiloxanes.

For instance, it has been proposed to emulsify silicone oils of certain viscosities with cationic surfactants and to incorporate these emulsions into fabric softener formulations which comprise further cationic surfactants (WO 00/71806 and WO 00/71807). In U.S. Pat. No. 4,961,753, hydrocarbon quats are combined with a mixture of high viscosity and low viscosity polysiloxanes.

Emulsions of hydrocarbon-based quats (silicone-free quaternary ammonium compounds with hydrocarbon radicals) with highly branched or crosslinked polydimethylsiloxane (PDMS) are claimed in U.S. Pat. No. 4,908,140. According to U.S. Pat. No. 4,978,462, it is advantageous also to add straight-chain PDMS to such a system.

The combination of hydrocarbon-based quats with OH-terminated polysiloxanes as a textile softener is claimed in WO 98/50502.

Combinations of hydrocarbon-based quats with siloxanes from the group of the unfunctionalized polydimethylsiloxanes, aminosiloxanes or polyethersiloxanes are described in WO 95/24460 as constituents of fabric softener formulations.

According to U.S. Pat. No. 5,852,110 and U.S. Pat. No. 6,090,885, aminosiloxane emulsions are prepared by alkaline polymerization in the presence of cationic surfactants.

Finally, GB 1 549 180 discloses the combination of emulsions of unfunctionalized polysiloxanes obtained by alkaline polymerization in the presence of cationic surfactants with further hydrocarbon quat. Alternatively, it is also said to be possible to use the hydrocarbon-based quats together with $\alpha,\omega$-diquaternary polysiloxanes or polyquaternary polysiloxanes or aminosiloxanes substituted in a comblike manner.

None of the proposals considered constitutes a satisfactory solution to the problem of achieving the soft hand, possible in principle by the use of silicones, of textile materials directly during the wash process with modern heavy-duty and light-duty detergent systems based on anionic surfactants.

WO 02/10256, WO 02/10257 and WO 02/10259 claim silicone materials which enable softening of textiles during the wash process with laundry detergent systems of this type. The US laid-open specification 2002/0103094 considers the use of the silicone materials mentioned in textile care formulations.

A further improvement in the performance of the above-described siloxane systems with regard to the achievable softness of the treated fibers, especially in the case of equal or improved substantivity (adhesion of the siloxane systems to the fiber), the flexibility in the formulation of the siloxane systems and the administration form, especially with a view to a reduction of the use amounts needed and the material costs, is very desirable.

It is thus an object of the invention to provide formulations based on polysiloxane, especially for the treatment of textiles and other natural and synthetic fiberlike materials, for example paper fibers and hair, which impart to such materials or substrates, preferably textile materials, a softness typical of silicones, an improved elasticity and reduced creasing tendency, especially in the presence of anionic surfactants or other ionic surface-active compositions for fiber pretreatment, as occur, for example, in the case of use in laundry detergent systems and in the case of finishing of pretreated fibers. At the same time, the formulations should have a high substantivity on the substrate surfaces.

It is a further object of the invention to provide for the use of these formulations as a constituent of separate softener systems after the washing of fibers has been performed, as a constituent of softener systems for nonwovens such as paper and textiles, as a constituent of systems for initial textile finishing, as an ironing aid and composition for prevention and reversal of textile creases and as a constituent of cosmetic systems for the treatment of hair and skin.

It is a further object of the invention to provide formulations based on polysiloxane which can be adjusted flexibly to the type of the substrates to be treated and the treatment conditions by simple variation of the composition ratios of the components present. In addition, the formulations should enable the amounts required to achieve the desired properties of the substrates to be treated and/or the use of expensive polysiloxane components, for example polysiloxane quats, to be reduced without a worsening in the desired properties of the substrates to be treated occurring.

It has been found that, surprisingly, particular multicomponent formulations of especially polysiloxane-containing compounds achieve the above object and constitute inexpensive and nevertheless exceptionally effective agents for the treatment of particular materials, in particular fiber materials.

The present invention thus provides a formulation which comprises:
a) at least one nitrogen-free polysiloxane compound,
b) at least one polyamino- and/or polyammonium-polysiloxane compound b1) and/or at least one amino- and/or ammonium-poly-siloxane compound b2)
c) optionally one or more silicone-free surfactants,
d) optionally one or more coacervate phase formation agents,
e) optionally one or more carrier substances.

The inventive formulation preferably contains, based on the total amount of components a) and b), from 5 to 99% by weight of component a) and from 1 to 95% by weight of component b). More preferably, the amount of component a) is from 20 to 90% by weight and the amount of component b) is from 10 to 80% by weight; particularly preferably the amount of component a) is from 30 to 90% by weight and the amount of component b) is from 10 to 70% by weight, based in each case on the total amount of components a) and b).

The optionally present carrier substances of component e) are preferably selected from solid carrier substances f) and/or liquid carrier substances g), which are described more precisely below.

The inventive formulation preferably contains from 0 to 1500, more preferably from 0 to 1000, more preferably from 0 to 500, even more preferably from 0 to 300 and most preferably from 0 to 150, parts by weight of the optionally present components c), d) and e), based on 100 parts by weight of components a) and b).

Component c) is added preferably in amounts of from 0 to 70, more preferably from 0 to 50 and particularly preferably from 0 to 30, parts by weight per 100 parts by weight of the total amount of components a) and b). If component c) is present in the inventive formulation, it is present in amounts of >0 part by weight, preferably >0.1 part by weight, per 100 parts by weight of the total amount of components a) and b).

Component d) is added preferably in amounts of from 0 to 10, more preferably from 0 to 3, particularly preferably from 0 to 1.5 and most preferably from 0 to 0.9, parts by weight per 100 parts by weight of the total amount of components a) and b). If component d) is present in the inventive formulation, it is present in amounts of >0, preferably >0.01, part by weight, preferably up to a maximum of 1 part by weight, per 100 parts by weight of the total amount of components a) and b).

Component f) is added preferably in amounts of from 0 to 710, more preferably from 0 to 300 and particularly preferably from 0 to 100, parts by weight per 100 parts by weight of the total amount of components a) and b). If component f) is present in the inventive formulation, it is present in amounts of >0 part by weight, preferably >5 parts by weight, per 100 parts by weight of the total amount of components a) and b).

Component g) is added preferably in amounts of from 0 to 710, more preferably from 0 to 300 and particularly preferably from 0 to 100, parts by weight per 100 parts by weight of the total amount of components a) and b). If component g) is present in the inventive formulation, it is present in amounts of >0 part by weight, preferably >5 parts by weight, per 100 parts by weight of the total amount of components a) and b).

Component e), i.e. component f) and/or g), is added preferably in amounts of from 0 to 1420, more preferably from 0 to 600 and particularly preferably from 0 to 200, parts by weight per 100 parts by weight of the total amount of components a) and b).

Component a) of the inventive formulation is a nitrogen-free polysiloxane compound. It preferably comprises straight-chain, cyclic, branched or partially crosslinked polydiorganosiloxanes in which the organo group is preferably selected from: $C_1$ to $C_6$ alkyl groups, polyalkyleneoxy groups whose end groups may be hydroxyl, ether or ester groups and which are preferably bonded to the silicon via alkylene groups, and aryl groups, and where the polydiorganosiloxanes may likewise optionally have functional groups, especially hydroxyl and alkoxy groups, on the silicon, with the exclusion of nitrogen-containing groups. The organo groups are more preferably selected from methyl, ethyl, butyl, phenyl, poly(ethyleneoxy) and copoly(ethyleneoxy)(propyleneoxy) groups. Greatest preference is given to polydialkylsiloxanes, especially polydimethylsiloxanes. The nitrogen-free, functionalized or unfunctionalized polysiloxane compounds as per component a), especially the polydimethylsiloxanes, appropriately have a viscosity in the range from 100 to 50 000 000 mPa·s, preferably from 10 000 to 20 000 000 mPa·s, more preferably from 10 000 to 10 000 000 mPa·s, more preferably between 100 000 and 10 000 000 mPa·s, such as between 100 000 and 1 000 000 mPa·s and between 1 000 000 and 10 000 000 mPa·s, at 25° C. and a shear rate gradient of $D=1\ s^{-1}$.

The polysiloxane compounds as per component a) which have functional groups are, for example, α,ω-dihydroxy-terminated polydimethylsiloxanes.

The amount of component a), based on the total amount of the formulation, is preferably in the range from 0.3% by weight to 99% by weight, preferably from 1.2% by weight to 90% by weight, more preferably from 1.8% by weight to 80% by weight and most preferably from 5% by weight to 70% by weight.

Examples of the polysiloxane compounds as per the definition of component a) are described, for example, in "Silicone Surfactants", ed.: R. M. Hill, Surfactant Science Series, Vol. 86, Marcel Dekker, Inc., 1999.

Preferred polysiloxane compounds as per the definition of component a) include, for example, silicone polymers of the formulae (II) to (III):

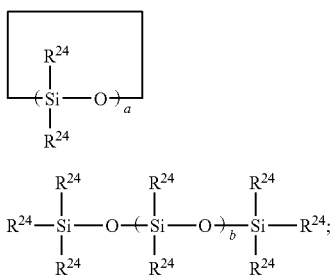

and mixtures thereof, in which $R^{24}$ is in each case independently selected from the group consisting of: hydroxyl groups, linear, branched or cyclic alkyl groups having from 1 to 22 carbon atoms, linear, branched or cyclic alkenyl groups having from 2 to 22 carbon atoms, linear, branched or cyclic alkoxy groups having from 1 to 8 carbon atoms, phenyl; alkylaryl groups having from 7 to 20 carbon atoms; arylalkyl groups having from 7 to 20 carbon atoms, a poly(ethylene oxide/propylene oxide) copolymer group of the general formula (IV):

$$—R^{25}—O(C_2H_4O)_c(C_3H_6O)_d—R^{26} \qquad (IV)$$

in which $R^{25}$ is a straight-chain, branched or cyclic alkanediyl group which has from 3 to 22 carbon atoms and may optionally be interrupted by one or more oxygen atoms, and $R^{26}$ is independently selected from the group consisting of hydrogen, alkyl having from 1 to 16 carbon atoms and an acetyl group, where the index a is appropriately selected in such a way that the viscosity of the nitrogen-free silicone polymer of the formula (II), for the derivatives of this class which are liquid at 25° C., is between 1 to 20 mPa·s and the index b is appropriately selected in such a way that the viscosity of the nitrogen-free silicone polymer of the formula (III), for the derivatives of this class which are liquid at 25° C., is between 1 to 50 000 000 mPa·s. The index "a" or the average degree of polymerization as $M_n$ is preferably from 3 to 6 and the index "b" or the average degree of polymerization as $M_n$ is preferably from 300 to 5000; where the viscosity values given in the present application are measured at a temperature of 25° C. and a shear rate gradient of $D=1 \ s^{-1}$; and where c+d=from 1 to 10 000 and c=from 1 to 10 000 and d=from 0 to 100, and the ethyleneoxy and propyleneoxy groups are arranged randomly or in block form, preferably randomly.

Examples of the nitrogen-free silicone polymers of the formula (III) are the Silwet® compounds from OSi Specialties of Crompton, Middlebury, Conn., USA, or Tegostab from Goldschmidt, Essen, or the SF PU foam stabilizer types from GE Bayer Silicones GmbH and Co KG, Leverkusen.

Further examples of the compounds of the formulae (II) and (III) are polydimethylsiloxane oils, for example from GE Bayer Silicones GmbH and Co. KG, of the Baysilone M series, or silicone oils of the 200 series from Dow Corning.

The preferred amount of component a) in the formulation, based on the total amount of the formulation, is from 5 to 99% by weight, preferably from 10 to 80% by weight, more preferably from 10 to 40% by weight.

The component b) used in accordance with the invention is at least one polyamino- and/or polyammonium-polysiloxane compound b1) and/or at least one amino- and/or ammonium-polysiloxane compound b2). The polyamino- and/or polyammonium-polysiloxane compound b1) is a copolymer compound which has amino and/or ammonium repeat units and polysiloxane repeat units in the polymer main chain. The amino units contain secondary and/or tertiary nitrogen atoms (2 or 3 organic radicals on the uncharged nitrogen atom). The ammonium units contain secondary, tertiary and/or quaternary, positively charged nitrogen atoms (2, 3 or 4 organic radicals on the nitrogen). The amino and/or ammonium repeat units may also serve heterocyclic radicals bonded into the polymer chain via two nitrogen atoms.

In contrast, component b2) comprises polysiloxane compounds which contain amino and/or ammonium groups in the pendent groups of the polysiloxane main chain. In other words, the amino and/or ammonium groups are not present in the main chain composed of polysiloxane repeat units.

The difference can be illustrated as follows:

polyamino- and/or polyammonium-polysiloxane compound b1):

-Amino/Ammonium-[Polyorganosiloxane-Amino/Ammonium-]$_n$Polyorgagosioxane-amino- and/or ammonium-polysiloxane compound b2):

In the inventive formulation, components b1) and b2) serve principally as a substantivity-imparting component.

In the inventive formulation, components b1) and b2) may be present alone or together. In a preferred embodiment, component b1) is, however, present alone in the inventive formulation, without component b2). In a likewise preferred embodiment, both component b1) and component b2) are present together.

Components b1) or b2) may be present together in any ratios relative to one another.

The polyamino- and/or polyammonium-polysiloxane compound b1) preferably comprises polysiloxane compounds which contain at least one unit of the formula (I):

$$—[Q—V]— \qquad (I)$$

in which Q is selected from the group consisting of:
—NR—,
—NR$^+$R$_2$—
a saturated or unsaturated diamino-functional heterocycle of the formulae:

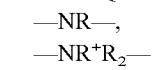

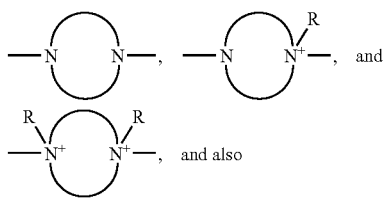

an aromatic diamino-functional heterocycle of the formula:

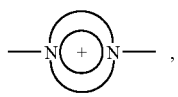

a trivalent radical of the formula:

a trivalent radical of the formula:

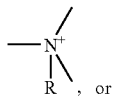, or a tetravalent radical of the formula

in which R is in each case hydrogen or a monovalent organic radical, where Q is not bonded to a carbonyl carbon atom, V is at least one constituent which is selected from the group consisting of $V^1$, $V^2$ and $V^3$, where $V^2$ is selected from divalent, straight-chain, cyclic or branched, saturated, unsaturated or aromatic hydrocarbon radicals which have up to 1000 carbon atoms (not counting the carbon atoms of the polysiloxane radical $Z^2$ defined below) and may optionally contain one or more groups selected from

—O—, —CONH—,

—CONR$^2$—, in which $R^2$ is hydrogen, a monovalent, straight-chain, cyclic or branched, saturated, unsaturated or aromatic hydrocarbon radical which has up to 100 carbon atoms, may contain one or more groups selected from —O—, —NH—, —C(O)— and —C(S)—, and may optionally be substituted by one or more substituents selected from the group consisting of a hydroxyl group, an optionally substituted heterocyclic group preferably containing one or more nitrogen atoms, amino, alkylamino, dialkylamino, ammonium, polyether radicals and polyether ester radicals, where, when a plurality of —CONR$^2$ groups is present, they may be the same or different, —C(O)— and —C(S)—, the $V^2$ radical may optionally be substituted by one or more hydroxyl groups, and the $V^2$ radical contains at least one —$Z^2$— group of the formula

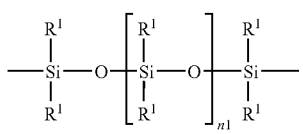

in which $R^1$ may be the same or different and is selected from the group consisting of: $C_1$ to $C_{22}$ alkyl, fluoro($C_1$-$C_{10}$)alkyl and $C_6$-$C_{10}$ aryl, and $n_1$=from 20 to 1000, $V^1$ is selected from divalent, straight-chain, cyclic or branched, saturated, unsaturated or aromatic hydrocarbon radicals which have up to 1000 carbon atoms and may optionally contain one or more groups selected from

—O—, —CONH—,

—CONR$^2$—, in which $R^2$ is as defined above, where the $R^2$ groups in the $V^1$ and $V^2$ groups may be the same or different, —C(O)—, —C(S)— and —$Z^1$—, where —$Z^1$— is a group of the formula

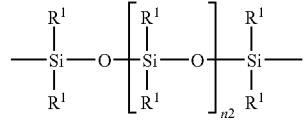

in which $R^1$ is as defined above, where the $R^1$ groups in the $V^1$ and $V^2$ groups may be the same or different, and $n_2$=from 0 to 19, and the $V^1$ radical may optionally be substituted by one or more hydroxyl groups, and $V^3$ is a trivalent or higher-valency, straight-chain, cyclic or branched, saturated, unsaturated or aromatic hydrocarbon radical which has up to 1000 carbon atoms, may optionally contain one or more groups selected from —O—, —CONH—, —CONR$^2$—, in which $R^2$ is as defined above, —C(O)—, —C(S)—, —$Z^1$— which is as defined above, —$Z^2$— which is as defined above and $Z^3$, where $Z^3$ is a trivalent or higher-valency organopolysiloxane unit, and may optionally be substituted by one or more hydroxyl groups, where, in said polysiloxane compound, in each case one or more $V^1$ groups, one or more $V^2$ groups and/or one or more $V^3$ groups may be present, with the proviso that said polysiloxane compound contains at least one $V^1$, $V^2$ or $V^3$ group which contains at least one —$Z^1$—, —$Z^2$— or $Z^3$ group, and that the tri- and tetravalent Q radicals either serve to branch the main chain formed from Q and V, so that the valencies which do not serve for bonding in the main chain bear further branches formed from —[Q—V]— units, or the tri- and tetravalent Q radicals are saturated with $V^3$ radicals within a linear main chain without formation of a branch, and wherein the positive charges resulting from ammonium groups are neutralized by organic or inorganic acid anions, and acid addition salts thereof.

The polysiloxane compounds which contain at least one unit of the formula (I) are terminated by monofunctional —Q—R and/or —V—R groups, i.e., for example, by amino groups. These arise by saturation of one of the two binding points of Q or V by a monovalent R group or hydrogen, which is as defined above, and are also referred to below as $V^{st}$ or $Q^{st}$. Instead of $V^{st}$, other unconverted reactive groups such as epoxy or haloalkyl groups may also be present.

In the context of the invention, the polysiloxane compounds which contain at least one unit of the formula (I) are also intended to include the case where only one —[Q—V]— unit is present, so that compounds of the formula R—V—[Q—V]—R or R—[Q—V]—Q—R, where R may also be replaced by H, are also included.

Suitable polyamino- and/or polyammonium-polysiloxane compounds b1) are described, for example, in WO 02/10257, WO 02/10259, DE-A 100 36 522, DE-A 100 36 532, DE-A 100 36 533 and the unpublished DE application 102 12 470.1. In addition, the compounds may also be according to U.S. Pat. No. 6,240,929.

The polysiloxane compounds which contain at least one unit of the formula (I) are, for example, linear polysiloxane copolymers of the general formula (I'):

—[Q—V]— (I')

in which Q is as defined above,

V is at least one $V^1$ group and at least one $V^2$ group, where $V^1$ and $V^2$ are each as defined above. In addition, V may also be trivalent or higher-valency, particularly trivalent, $V^3$ radicals. In this case, tri- or tetravalent Q units, as defined above, are also present, and the trivalent or higher-valency $V^3$ radicals and the tri- or tetravalent Q units are saturated exclusively by one another within the linear main chain to form cyclic structures, as illustrated in more detail below. However, this case is less preferred.

In a preferred embodiment of the polyamino- and/or polyammonium-polysiloxane copolymers b1) of the formulae (I) or (I'), Q is therefore selected from the group consisting of:

—NR—,
—NR⁺R2-
a saturated or unsaturated diamino-functional heterocycle of the formulae:

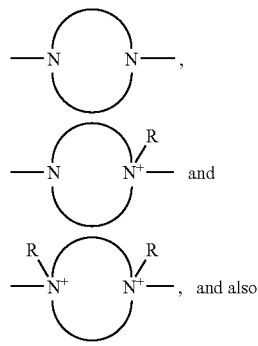

an aromatic diamino-functional heterocycle of the formula:

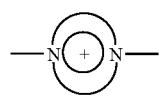

in which R is as defined above, and V is selected from $V^1$ and $V^2$.

In the general formulae (I) and (I'), the molar ratio of the $V^1$ and $V^2$ groups in the polysiloxane compounds $V^2/V^1$ may in principle assume any value. The invention thus also includes the case in which the polysiloxane compound of the formulae (I) or (I') contains only $V^2$ units, i.e. the polysiloxane compound has the formula —[Q—$V^2$]—. The invention also embraces the case in which the polysiloxane compound contains only $V^1$ units. However, in this case, the $V^1$ units have to contain $Z^1$-siloxane units.

In a preferred embodiment of the invention, however, the polysiloxane compound of the formulae (I) or (I') contains both $V^2$ and $V^1$ units.

In a further preferred embodiment of the present invention, the molar ratio of the $V^1$ and $V^2$ groups in the polysiloxane compounds of the general formulae (I) and (I') is:

$V^2/V^1=1$.

Such linear amine and tetraorganoammonium compounds have been described, for example, in WO 02/10257, WO 02/10259, EP 282720 or U.S. Pat. No. 5,981,681. Particular preference is given to the polysiloxanes of WO 02/10259 and WO 02/10257, and reference is made here explicitly to the polysiloxane polymers defined in claims 1 which form part of the disclosure content of the present application.

In a further embodiment of the linear polysiloxane compounds of the formula (I) or (I'), $V^2/V^1$ does not equal 1; preferably, $V^2/V^1$ is <1, more preferably <0.9; even more preferably, $V^2/V^1$ fulfills the relationship $0.0005 < V^2/V^1 < 0.5$, more preferably $0.0005 < V^2/V^1 < 0.3$.

The R group is preferably selected from the $R^2$ groups.

In a preferred embodiment of the invention, Q is a divalent radical and is selected in the formulae (I) or (I') from the group consisting of:

—NR—,
—NR⁺R2- a quaternized imidazole unit of the structure

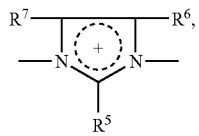

a quaternized pyrazole unit of the structure

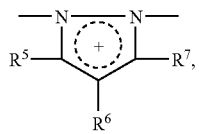

a diquaternized piperazine unit of the structure

a monoquaternized piperazine unit of the structure

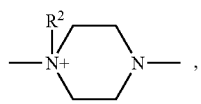

a monoquaternized piperazine unit of the structure

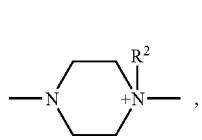

a diquaternized unit of the structure

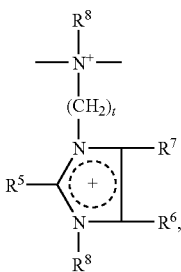

a monoquaternized unit of the structure a monoquaternized unit of the structure a diquaternized unit of the structure a monoquaternized unit of the structure

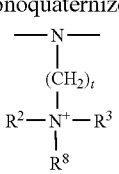

and a monoquaternized unit of the structure

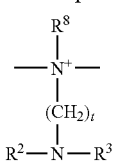

in which t is from 2 to 10,

R is as defined above, preferably $R^2$, $R^2$ is as defined above, and the definition of $R^2$ and the definition of the above $R^2$ group may be the same or different, $R^3$ has the definition of $R^2$, where $R^2$ and $R^3$ may be the same or different, or $R^2$ and $R^3$ together with the positively charged nitrogen atom form a five- to seven-membered heterocycle which may optionally additionally have one or more nitrogen, oxygen and/or sulfur atoms, $R^5$, $R^6$, $R^7$ may be the same or different and are selected from the group consisting of: H, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the —$NHR^w$ type in which $R^w$ is H, alkyl group, monohydroxyalkyl group, polyhydroxyalkyl group, acetyl group, ureido group, and in each case two of the adjacent $R^5$, $R^6$ and $R^7$ radicals with the carbon atoms binding them to the heterocycles may form aromatic five- to seven-membered rings, and $R^8$ has the definition of $R^2$, where $R^8$ and $R^2$ may be the same or different.

In the case that Q is a trivalent radical of the formulae

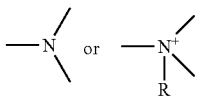

or a tetravalent radical

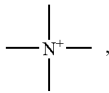

these radicals in the linear copolymers of the formula (I'), as mentioned above, do not serve to branch the polysiloxane copolymers, but rather these radicals are bonded exclusively to especially trivalent $V^3$ radicals to form cyclic structures which are part of the linear main chain, for example a structural element of the formula:

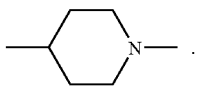

In a preferred embodiment of the polysiloxane compounds of the formula (I) or (I') as component b1), $V^2$ is a group of the formula

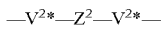

in which $Z^2$ is as defined above and $V^{2*}$ is a divalent, straight-chain cyclic or branched, saturated, unsaturated or aromatic hydrocarbon radical which has up to 40 carbon atoms and may optionally contain one or more groups selected from —O—, —CONH—, —$CONR^2$— in which $R^2$ is as defined above, —C(O)— and —C(S)—, and the $V^{2*}$ radical may optionally be substituted by one more hydroxyl groups.

In the aforementioned embodiment, the inventive linear polysiloxane copolymer may have the following repeat units:

$[V^2{*}-Z^2-V^2{*}-Q]-$, preferably together with $-[V^1-Q]-$.

The molar ratio of the repeat units $[V^2{*}-Z^2-V^2{*}-Q]-$ to $-[V^1-Q]-$, i.e. the $V^2/V^1$ ratio, may, as mentioned above, be 1, but is, in one embodiment, preferably unequal to 1, more preferably <0.9, even more preferably <0.8, even more preferably <0.3. In the cases where $V^2/V^1<1$, the linear polysiloxane copolymers $-[Q-V]-$ mentioned necessarily contain blocks which contain more than one $-[V^1-Q]-$ unit joined together.

As is explained in detail below in connection with the process for preparing the above-described linear polysiloxane-copolymers, the blocklike sequences which have more than one $-[V^1-Q]-$ unit joined together may, depending on the preparation method, be bonded regularly with the $V^2-Q$ units or irregularly with the $V^2-Q$ units.

This means the following:

In the case of regular bonding, in which, for example, a prepolymer corresponding to the $-[Q-[V1-Q]_x-$ group is reacted with monomer units corresponding to $V^2$ in a molar ratio of 1:1, the linear polysiloxane copolymers can be represented as follows:

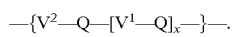

In this formula, x may be from 2 to 2000 and is the median of the distribution. The linear polysiloxane copolymers represented by the formula $-\{V^2-Q-[V^1-Q]_x-\}-$ are characterized in that they have substantially no $-V^2-Q-$ units joined to one another, or, in other words, two $-V^2-Q-$ units are always interrupted by at least one $-V^1-Q-$ unit.

In the case of irregular bonding, in which, for example, monomers corresponding to Q units are reacted with monomer units corresponding to $V^1$ and monomer units corresponding to $V^2$ in a ratio of $Q/(V^1+V^2)$, where, for example, $V^2/V^1<1$, preferably <0.5, of 1:1, the linear polysiloxane copolymers can be represented as follows:

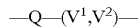

in which V the $V^2/V^1$ ratio is <1 or <0.5. In this formula, the $V^1$ and $V^2$ groups are distributed randomly over the copolymer chain. In contrast to the linear polysiloxane copolymers prepared by the regular bonding, this copolymer may also have adjacent $-Q-V^2-$ units.

In a preferred embodiment of the polysiloxane compound of the formula (I) or (I') used in accordance with the invention as component b1), the $V^1$ group is selected from divalent, straight-chain, cyclic or branched, saturated, unsaturated or aromatic hydrocarbon radicals which have up to 600, preferably up to 400, carbon atoms and may optionally contain one or more groups selected from $-O-$, $-CONH-$, $-CONR^2-$ in which $R^2$ is as defined above, $-C(O)-$, $-C(S)-$ and $-Z^1-$, where $-Z^1-$ is a group of the formula

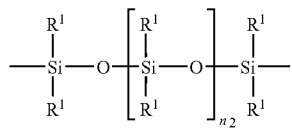

in which $R^1$ is $C_1$-$C_{18}$ alkyl which may optionally be substituted by one or more fluorine atoms or is phenyl, and $n_2$ is as defined above.

In a further preferred embodiment of the polysiloxane compounds of the formula (I) or (I') as component b1), the Q group is selected from:

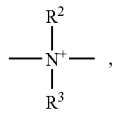

a quaternized imidazole unit of the structure,

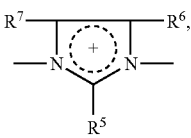

a quaternized pyrazole unit of the structure

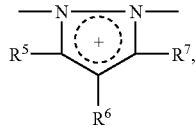

a diquaternized piperazine unit of the structure

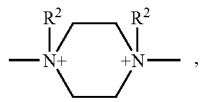

a monoquaternized piperazine unit of the structure

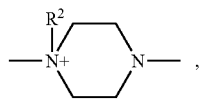

a monoquaternized piperazine unit of the structure

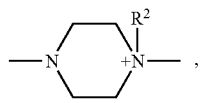

a monoquaternized unit of the structure

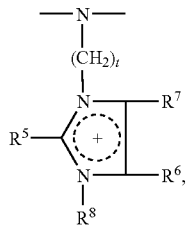

in which $R^2$, $R^3$, $R^4$, $R^5$, $R^6$, $R^7$ and $R^8$ are each as defined above.

In a further preferred embodiment of the linear polysiloxane compounds of the formula (I') as component b1) of the present invention, the molar ratio $V^2/V^1$ fulfills the relationship $$0.0005<V^2/V^1<0.5(=2<V^1/V^2<2000)$$

more preferably the relationship $$0.005 < V^2/V^1 < 0.4 (= 2.5 < V^1/V^2 < 200)$$

even more preferably the relationship $$0.01 < V^2/V^1 < 0.3 (= 3.3 < V^1/V^2 < 100).$$

In the formulae (I) and (I'), preferably:

$R^1 = C_1$ to $C_{18}$ alkyl, in particular methyl, ethyl, trifluoropropyl and phenyl, $n_1$=from 20 to 400, more preferably from 20 to 300, especially from 20 to 200. In a further preferred embodiment, $n_1$ is between 20 and 50 or between 80 and 200. The number $n_1$ is the average degree of polymerization from $M_n$ of the diorganosiloxy units in the $Z^2$ group.

$n_2$=from 0 to 15, more preferably from 0 to 10, especially from 0 to 5, more especially 0. The number $n_2$ is the average degree of polymerization from $M_n$ of the diorganosiloxy units in the $Z^1$ group.

$V^{2*}$=a divalent straight-chain, cyclic or branched, saturated, unsaturated $C_3$ to $C_{16}$ hydrocarbon radical or aromatic $C_8$ to $C_{20}$ hydrocarbon radical which may optionally contain one or more groups selected from —O—, —CONH—, —CONR²—, —C(O)—, —C(S)— and may be substituted by one or more OH groups, where $R^2$ is as defined above.

$$Q = -\underset{\underset{R^3}{|}}{\overset{\overset{R^2}{|}}{N^+}}-,$$

a quaternized imidazole unit of the structure a diquaternized piperazine unit of the structure a monoquaternized piperazine unit of the structure a monoquaternized piperazine unit of the structure a monoquaternized unit of the structure in which $R^2$, $R^3$, $R^4$, $R^5$, $R^6$, $R^7$ and $R^8$ are each as defined above.

More preferably, $V^{2*}$ is a divalent straight-chain, cyclic or branched, saturated, unsaturated or aromatic hydrocarbon radical which has up to 16 carbon atoms, may be substituted by one or more groups selected from —O—, —CONH—, —CONR²— in which $R^2$ is as defined above, —C(O)—, —C(S)— and may be substituted by one or more hydroxyl groups. Even more preferably, —$V^{2*}$— is selected from groups of the formulae:

—(CH₂)₃OCH₂CHCH₂—    —(CH₂)₃OCH₂CH₂—
               |                             |
              OH                      CH₂OH

—(CH₂)₂—[cyclohexyl with OH and CH₃ substituents]

—(CH₂)₂—[cyclohexyl with OH substituent]

—CH₂CH(CH₃)—[cyclohexyl with OH and CH₃ substituents]

—CH₂CH(CH₃)—[cyclohexyl with CH₃ and OH substituents]

—(CH₂)₂—,    —(CH₂)₃—,    —(CH₂)₄—,

—(CH₂)₅—,    —(CH₂)₆—,

—CH=CHCH₂—,    —CH=CHCH₂CH₂—,

—CH₂CH₂CH₂OC(O)CH₂—,

—CH₂CH₂CH₂OC(O)CH₂CH₂—,

—CH=CHCH₂OC(O)CH₂—,

—CH=CHCH₂OC(O)CH₂CH₂—,

CH₃
                                        |
—CH₂CH₂CH₂(OCH₂CH₂)ᵥ(OCH₂CH)ᵥᵥOC(O)CH₂—

CH₃
                                              |
—CH₂CH₂CH₂(OCH₂CH₂)ᵥ(OCH₂CH)ᵥᵥOC(O)CH₂CH₂—

CH₃
                             |
—CH=CHCH₂(OCH₂CH₂)ᵥ(OCH₂CH)ᵥᵥOC(O)CH₂—

CH₃
                                 |
—CH=CHCH₂(OCH₂CH₂)ᵥ(OCH₂CH)ᵥᵥOC(O)CH₂CH₂—

CH₃
                                    |
—CH=CHCH₂CH₂(OCH₂CH₂)ᵥ(OCH₂CH)ᵥᵥOC(O)CH₂—

-continued

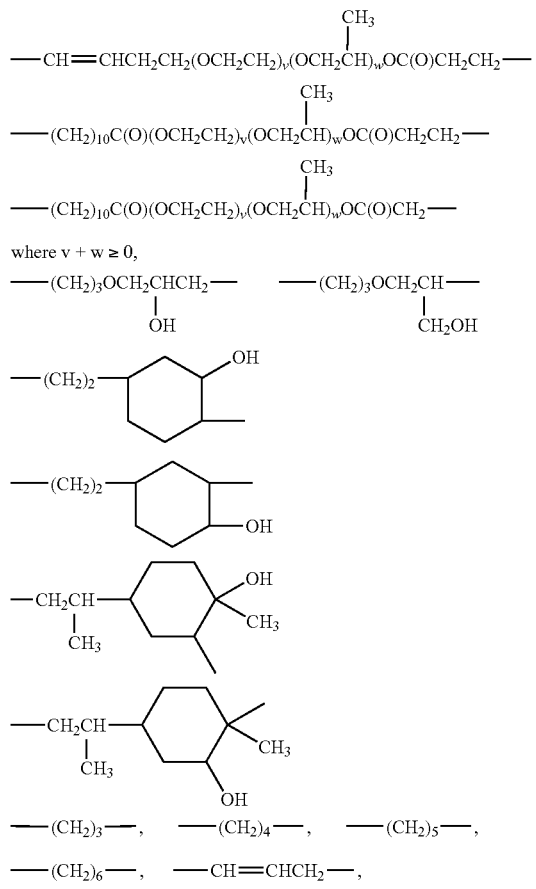

where v + w ≥ 0, $R^2$ is preferably: H,
—$CH_3$, —$CH_2CH_3$, —$(CH_2)_2CH_3$, —$(CH_2)_3CH_3$,
—$(CH_2)_5CH_3$, —$CH_2CH_2OH$,

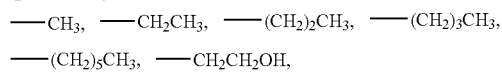

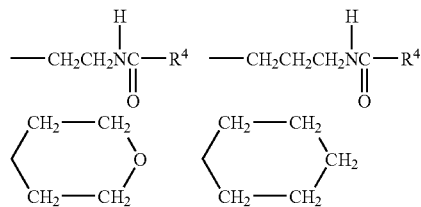

where $R^4$=straight-chain, cyclic or branched $C_1$ to $C_{18}$ hydrocarbon radical which may be substituted by one or more groups selected from —O—, —NH—, —C(O)— and —C(S)— and may be substituted by one or more OH groups, especially unsubstituted $C_5$ to $C_{17}$ hydrocarbon radicals which derive from the corresponding fatty acids or else hydroxylated $C_3$ to $C_{17}$ radicals which can be traced back to hydroxylated carboxylic acids, especially saccharide carboxylic acids, and quite especially

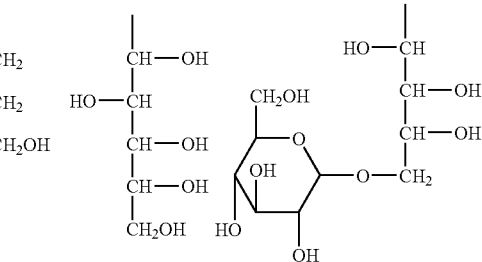

Moreover, $R^2$ is preferably:

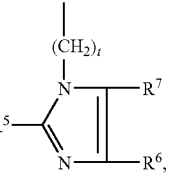

in which t, $R^5$ and $R^8$ are each as defined above,

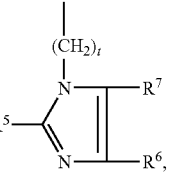

in which t, $R^5$ to $R^7$ are each as defined above,

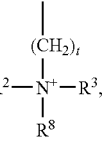

in which t, $R^2$, $R^3$ and $R^8$ are each as defined above.

$V^1$ is preferably
—$R^9$—, in which $R^9$ is a divalent, saturated or mono- or polyunsaturated, straight-chain or branched hydrocarbon radical having from two to 25 carbon atoms,
—$(CH_2)_uC(O)O$—$[(CH_2CH_2O)_q$—$(CH_2CH(CH_3)O_r]$—$C(O)(CH_2)_u$—
—$(CH_2)_uC(O)O$—$R^9$—O—$C(O)(CH_2)_u$— in which $R^9$ is as defined above,
—$(CH_2)_u$—$R^{10}$—$(CH_2)_u$— in which $R^{10}$ is an aromatic group,
—$[CH_2CH_2O]_q$—$[CH_2CH(CH_3)O]_r$—$CH_2CH_2$—,
—$CH(CH_3)CH_2O[CH_2CH_2O]_q$—$[CH_2CH(CH_3)O]_r$—$CH_2CH(CH_3)$—
—$CH_2CH(OH)CH_2$—,
—$CH_2CH(OH)(CH_2)_2CH(OH)CH_2$—,
—$CH_2CH(OH)CH_2OCH_2CH(OH)CH_2OCH_2CH(OH)CH_2$— and
—$CH_2CH(OH)CH_2O$—$[CH_2CH_2O]_q$—$[CH_2CH(CH_3)O]_r$—$CH_2CH(OH)CH_2$— in which u is from 1 to 3, q and r are each from 0 to 200, preferably from 0 to 100, more preferably from 0 to 70 and particularly preferably from 0 to 40, and q+r>0.

Preferred variants of $V^1$ are structures of the formula:
—$CH_2C(O)O$—$[CH_2CH_2O]_q$—$[CH_2CH(CH_3)O]_r$—$C(O)CH_2$—,
—$CH_2CH_2C(O)O$—$[CH_2CH_2O]_q$—$[CH_2CH(CH_3)O]_r$—$C(O)CH_2CH_2$—,
—$CH_2CH_2CH_2C(O)O$—$[CH_2CH_2O]_q$—$[CH_2CH(CH_3)O]_r$—$C(O)CH_2CH_2CH_2$—, esterified alkylene, alkenylene, alkynylene units, especially of the structures
—$CH_2C(O)O$—$[CH_2]_o$—$OC(O)CH_2$—,
—$CH_2CH_2C(O)O$—$[CH_2]_o$—$OC(O)CH_2CH_2$—,
—$CH_2CH_2CH_2C(O)O$—$[CH_2]_o$—$OC(O)CH_2CH_2CH_2$—
—$CH_2C(O)O$—$CH_2C\equiv CCH_2$—$OC(O)CH_2$—,
—$CH_2CH_2C(O)O$—$CH_2C\equiv CCH_2$—$OC(O)CH_2CH_2$—,
—$CH_2CH_2CH_2C(O)O$—$CH_2C\equiv CCH_2$—$OC(O)CH_2CH_2CH_2$—,
—$CH_2C(O)O$—$CH_2CH=CHCH_2$—$OC(O)CH_2$—,
—$CH_2CH_2C(O)O$—$CH_2CH=CHCH_2$—$OC(O)CH_2CH_2$—,
—$CH_2CH_2CH_2C(O)O$—$CH_2CH=CHCH_2$—$OC(O)CH_2CH_2CH_2$—, alkylene, alkenylene, alkynylene and aryl units, especially of the structures:

—$[CH_2]o$- where o=from 2 to 6,
—$CH_2C\equiv CCH_2$—, —$CH_2CH=CHCH_2$—, —$CH(CH_3)CH_2CH_2$—,

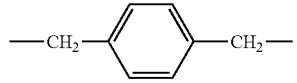

polyalkylene oxide units, especially of the structures
—$[CH_2CH_2O]_q$—$[CH_2CH(CH_3)O]_r$—$CH_2CH_2$—,
—$CH(CH_3)CH_2O[CH_2CH_2O]_q$—$[CH_2CH(CH_3)O]_r$—$CH_2CH(CH_3)$— with mono-, di- or polyhydroxy-functional units, especially of the structures
—$CH_2CH(OH)CH_2$—, —$CH_2CH(OH)(CH_2)_2CH(OH)CH_2$—,
—$CH_2CH(OH)CH_2OCH_2CH(OH)CH_2OCH_2CH(OH)CH_2$—,
—$CH_2CH(OH)CH_2O$—$[CH_2CH_2O]_q$—$[CH_2CH(CH_3)O]_r$—$CH_2CH(OH)CH_2$— where q=from 0 to 200, r=from 0 to 200.

Preferably, q=from 1 to 50, in particular from 2 to 50, especially from 1 to 20, very especially from 1 to 10, and also 1 or 2, r=from 0 to 100, in particular from 0 to 50, especially from 0 to 20, very especially from 0 to 10, and also 0 or 1 or 2.

The linear polysiloxanes of the formulae (I) or (I') may be prepared, for example, by a process in which
a) at least one amine compound selected from a diamine compound and/or a primary or secondary monoamine compound is reacted with at least two difunctional organic compounds capable of reaction with the amino functions of the amine compound, the molar ratio of the organic compounds being selected in such a way that the desired $V^2/V^1$ ratio is obtained,
b) at least two mol of an amine compound selected from a diamine compound and/or a primary or secondary monoamine compound is reacted with one mole of a difunctional organic compound capable of reaction with the amino functions of the amine compound to form a diamine compound (monomer) which is subsequently reacted with at least one amine compound selected from a diamine compound and/or a primary or secondary monoamine compound and at least one further difunctional organic compound capable of reaction with the amino function of the amine compounds,
c) an amine compound selected from a diamine compound and/or a primary or secondary monoamine compound is reacted with a difunctional organic compound capable of reaction with the amino functions of the amine compounds to form a diamine compound (amino-terminated oligomer) which is subsequently reacted with at least one difunctional organic compound capable of reaction with the amino functions of the diamine compounds,
d) an amine compound selected from a diamine compound and/or a primary or secondary monoamine compound is reacted with a difunctional organic compound capable of reaction with the amino functions of the amine compound to form a difunctional compound capable of reaction with amino functions (difunctional oligomer) which is subsequently reacted with at least one amine compound selected from a diamine compound and/or a primary or secondary monoamine compound and at least one further compound capable of reaction with amino functions, where monofunctional, preferably tertiary, monoamines or suitable monoamines incapable of chain propagation and/or monofunctional compounds capable of reaction with amino functions may optionally be added as chain terminators, and the stoichiometry of the amino functions and of the functional groups capable of reaction with amino functions in the last stage of the reaction is always about 1:1, and where any amino functions present may be protonated or quaternized.

Variant a), in which at least one diamine compound selected from a diamine compound and/or a primary or secondary monoamine compound is reacted with at least two difunctional organic compounds capable of reaction with the amino functions of the amine compound, the molar ratio of the organic compounds being selected such that the desired $V^2/V^1$ ratio, for example <0.5, is fulfillled, can thus be represented schematically, for example, as follows:

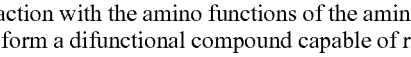
or
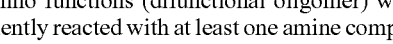

where —[N—N]—, can include an acyclic diamine corresponding to the definition of Q or a $V^1$-containing diamine —[N—$V^1$—N]— or a $V^2$-containing diamine —[N—$V^2$—N]—, in particular —[N—$V^{2*}$—$Z^2$—$V^{2*}$—N]—, the latter giving rise in each case to two Q units and one $V^1$ unit or two $V^2$ units, and -[$v^1$]- and —[$V^2$]— are intended to represent the monomers corresponding to the repeat units $V^1$ and $V^2$, and —[N]— is a primary or secondary monoamine suitable for chain propagation.

From the —[N—N]— and/or —[N]— units, at least one relatively highly alkylated amine or a quaternary ammonium unit Q is formed, and secondary or tertiary amino functions formed in the polymerization may optionally be protonated or quaternized in a separate step after the polymerization. Preference is given to the formation of quaternary ammonium units.

Preferred examples of —[N—N]— are as described in more detail below: piperazine and imidazole; preferred diamine units —[N—V$^1$—N]— include, for example: polymethylenediamines such as tetramethylhexamethylenediamine, α,ω-diamino-terminated polyethers, for example Jeffamines, etc.

Preferred diamine units —[N—V$^{2*}$—Z$^2$—V$^{2*}$—N]— include, for example, reaction products of α,ω-dihydropolydialkylsiloxanes with allylamines.

Preferred examples of —[N]— are as described in more detail below, for example dimethylamine.

The use of diamines —[N—N]— is preferred in principle.

Preferred —[V$^1$]— monomers include, for example, epichlorohydrin, bischloroalkyl esters, bisepoxides or bisacrylates. It is also possible with preference to use mixtures of the —[V$^1$]— monomers mentioned, for example mixtures of epichlorohydrin, bischloroalkyl esters or bisepoxides.

Preferred —[V$^2$]— monomers are monomers of the formula —[V$^{2*}$—Z$^2$—V$^{2*}$] in which Z$^2$ is as defined above and —[V$^{2*}$] is a functionalized group corresponding to the V$^{2*}$ repeat unit. Preferred —[V$^{2*}$] monomers for the formation of the V$^2$ repeat units are in particular α,ω-diepoxy-terminated polydialkylsiloxanes.

Variant b) can be carried out either with diamines —[N—N]— or suitable monoamines —[N]— and can be represented schematically, for example, as follows:

Variant b1)

Step 1): 2-[N—N]— + —[V$^2$]— or —[V$^1$]— → —[N—N—V$^1$—N—N]— or

—[N—N—V$^2$—N—N]—

Step 2.1): —[N—N—V$^2$—N—N]— → —[V$^1$]— + —[N—N]— →,

Step 2.2): —[N—N—V$^1$—N—N]— + —[V$^2$]— + —[N—N]— →, where the stoichiometry V$^2$/V$^1$ is established as desired.

With regard to the —[N—N]—, —[V$^1$]— and —[V$^2$]— monomer units used with preference, the same applies as was stated for step a).

Variant b2)

Step 1): 2-[N]] + —[V$^2$]— or —[V$^1$]— → —[N—V$^1$—N]— or —[N—V$^2$—N]—

Step 2.1): —[N—V$^2$—N]— + —[V$^1$]— + —[N]— →,

Step 2.2): —[N—V$^1$—N]— + —[V$^2$]— + —[N]— →, where this variant, as mentioned above, can be carried out only with primary or secondary monoamines and where, with regard to the —[N]—, —[V$^1$]— and —[V$^2$]— monomer units used with preference, the same applies as was stated for step a).

Variant c) can be represented schematically, for example, as follows:

Variant c1)

Step 1): —[N—N]— + —[V$^1$]— → —[N—N—(V$^1$—N—N)$_x$]—

Step 2): —[N—N—(V$^1$—N—N)$_x$]— + —[V$^2$]— → where, with regard to the —[N—N]—, —[V$^1$]— and —[V$^2$]— monomer units used with preference, the same applies as was stated for step a).

Variant c2)

Step 1): —[N]— + —[V$^1$]— → —[N—(V$^1$—N)$_x$]—

Step 2): —[N—(V$^1$—N)$_x$]— + —[V$^2$]— → where, with regard to the —[N]—, —[V$^1$]— and —[V$^2$]— monomer units used with preference, the same applies as was stated for step a).

Variant d) can be represented schematically, for example, as follows:

Variant d1)

Step 1): —[V$^1$]— + —[N—N]— → [V$^1$—(N—N—V$^1$)$_x$]—

Step 2): —[V$^1$—(N—N—V$^1$)$_x$]— + —[V$^2$]— + —[N]— or —[N—N]— → where, with regard to the —[N—N]—, —[V$^1$]— and —[V$^2$]— monomer units used with preference, the same applies as was stated for step a).

Variant d2)

Step 1): —[V$^1$]— + —[N]— → —[V$^1$—(N—V$^1$)$_x$]—

Step 2: —[V$^1$—(N—V$^1$)$_x$]— + —[V$^2$]— + —[V$^2$]— + —[N]— or —[N—N]— → where, with regard to the —[N—N]—, —[V$^1$]— and —[V$^2$]— monomer units used with preference, the same applies as was stated for step a).

For all variants represented schematically above, it is also possible to use mixtures of monoamines —[N]— and diamines —[N—N]—.

Particular preference is given to selecting the functional groups of the difunctional compounds capable of reaction with amino functions from the group consisting of epoxy groups and haloalkyl groups.

A preferred starting point for the syntheses of the polysiloxane copolymers of the formulae (I) and (I') used in accordance with the invention is α,ω Si—H functionalized siloxanes of the general structure

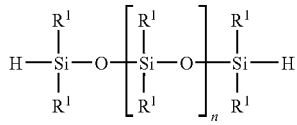

where R$^1$ is as defined above and n, depending on the desired V$^1$ or V$^2$ repeat units, is n$_1$ or n$_2$ which are as defined above. When they are not commercially available, these siloxanes may be prepared by known processes, for example by equilibration (Silicone, Chemie und Technologie [Silicones, chemistry and technology], Vulkan-Verlag, Essen 1989, p. 82-84).

The precursors of the structural elements V$^{2*}$ and Q may be prepared, for example, by two routes.

On the one hand, it is possible first to bind unsaturated structures bearing tertiary amino functions, for example N,N-dimethylallylamine, by hydrosilylation directly to the siloxane in α,ω arrangement. This process is common knowledge (B. Marciniec, Comprehensive Handbook on Hydrosilylation, Pergamon Press, Oxford 1992, p. 122-124).

On the other hand, it is preferred initially to generate by hydrosilylation reactive (α,ω-functionalized intermediates which can subsequently be converted to α,ω)-ditertiary amino structures or directly to the inventive quaternary ammonium structures. Suitable starting materials for generating reactive intermediates are, for example, halogenated alkenes or alkynes, especially allyl chloride, allyl bromide, chloropropyne and chlorobutyne, unsaturated halocarboxylic esters, especially allyl chloroformate, propargyl chloroformate, allyl 3-chloropropionate and propargyl 3-chloropropionate and epoxy-functional alkenes, for example vinylcyclohexene oxide and allyl glycidyl ether. The general performance of hydrosilylations with representatives of the substance groups mentioned is likewise known (B. Marciniec, Comprehensive Handbook on Hydrosilylation, Pergamon Press, Oxford 1992, p. 116-121, 127-130, 134-137, 151-155).

In a subsequent step, the reactive intermediates may then be reacted with compounds bearing secondary amino functions. Suitable representatives are N,N-dialkylamines, for example dimethylamine, diethylamine, dibutylamine, diethanolamine and N-methylglucamine, cyclic secondary amines, for example morpholine and piperidine, amino amides bearing secondary amino functions, for example the reaction products of diethylenetriamine or dipropylenetriamine with lactones such as γ-butyrolactone, δ-gluconolactone and glucopyranosylarabonolactone (DE-A 43 18 536, examples 11a, 12a, 13a) or secondary-tertiary diamines, for example N-methylpiperazine. It is especially preferred to utilize appropriate imidazole or pyrazole derivatives, especially imidazole and pyrazole, for the introduction of tertiary amino functions.

Suitable partners for the epoxide derivatives which are used with preference in one embodiment are particularly the secondary-tertiary diamines mentioned, and also imidazole and pyrazole. In this way, it is possible to direct the alkylations to the nitrogen atoms bearing hydrogen atoms regioselectively and without additional complexity.

To ensure a quantitative conversion of the reactive moieties to tertiary amino structures, the amines are used in a ratio of $1 \leq \Sigma$ secondary amino groups:reactive groups $\leq 10$, preferably from 1 to 3, especially from 1 to 2, very especially 1. Amine excesses have to be removed in some cases.

The bonding of the above-described α,ω-ditertiary aminosiloxanes to —[$V^1$]— monomer units corresponding to $V^1$ or a prepolymer unit —[$V^1$—(Q—$V^1$)$_x$]— leads to the formation of further relatively highly alkylated amino units or quaternary ammonium units and may in turn be effected in two advantageous ways.

On the one hand, preference is given to separately generating a strongly hydrophilic, polyquaternary, difunctional precondensate —[$V^1$—(Q—$V^1$)$_x$]— which is combined at a suitable time with the α,ω-ditertiary aminosiloxanes and reacts to give the polyamino or polyquaternary siloxane copolymer.

The preparation of highly charged, difunctional prepolymers of different chain length —[$V^1$—(Q—$V^1$)$_x$]— is described by way of example in WO 99/14300 (examples 1 to 7, table 11). Depending on the molar ratio of $V^1$ and the parent amine of Q, it is possible to generate a prepolymer terminated either by amino groups or by other reactive groups.

In the case of the binding of a prepolymer terminated by amino groups —[N—($V^1$—N)$_x$]— to the amine function of an α,ω-ditertiary aminosiloxane structure, it is possible, for example, to use an alkylating or quaternizing difunctional monomer —[$V^1$]— corresponding to the repeat unit $V^1$, selected, for example, from bisepoxides, epichlorohydrin, bishaloalkyl compounds. It need not be mentioned here that different $V^1$ groups can result in the prepolymer and in the linking group between prepolymer and α,ω-ditertiary aminosiloxane structure.

In the case of a prepolymer terminated by reactive groups, such as —[$V^1$—(Q—$V^1$)$_x$]—, direct bonding to the amine function of the α,ω-ditertiary aminosiloxane structure may be effected without a further linker, since an excess of the $V^1$-generating component has already been used in the prepolymer synthesis.

Alternatively to the separate preparation of a precondensate —[$V^1$—(Q—$V^1$)$_x$]—, highly charged blocks can be formed in parallel to the incorporation into the copolymer. This means that the α,ω-ditertiary aminosiloxane can be initially charged together with the starting components for the formation of —[$V^1$—(Q—$V^1$)$_x$]—, i.e., for example, —[$V^1$]— and mono- or diamines of the abovementioned definition —[N]— and/or —[N—N]—, and reacted.

Finally, it is possible to meter the α,ω-ditertiary aminosiloxane with a long-chain siloxane unit $Z^2$ or short-chain siloxane unit $Z^1$, or the α,ω-difunctional siloxane —[N—$V^{2*}$—$Z^2$—$V^{2*}$—N]— or —[N—$V^1$—N]—, stepwise over a period of time into the initially charged components for the formation of —[$V^1$—(Q—$V^1$)$_x$]—, or else, conversely, to add these components stepwise to the α,ω-ditertiary aminosiloxane or α,ω-difunctional siloxane.

A preceding preparation of prepolymers terminated by amino groups, for example —[N-($V^1$—N)$_x$]—, opens up the possibility of performing the copolymer formation directly with suitable reactive intermediates, for example epoxy derivatives.

It is likewise preferred to initially charge the reactive intermediates and the starting components for the formation of —[$V^1$—(Q—$V^1$)$_x$]— together and subsequently to react them.

Finally, it is possible to meter the reactive intermediates stepwise over a period of time into the initially charged components for the formation of —[$V^1$—(Q—$V^1$)$_x$]—, or else, conversely, to add these components stepwise to the reactive intermediate.

Irrespective of the selection of the above-described reaction paths and the closely related question of whether amino units terminate the siloxane or else the prepolymer first, the overall stoichiometry is selected such that the sum of the amino functions and of the groups reactive with them is about 1:1.

In the context of the invention, it is possible to deviate from this preferred overall stoichiometry. However, products are then obtained which no longer have the envisaged length of the highly charged, hydrophilic block —[$V^1$—(Q—$V^1$)$_x$]— and additionally leave behind an excess of an unreacted starting component.

In addition to the overall stoichiometry, considered above, of the reaction, the selection of the component(s) forming the $V^1$ repeat unit is of great significance for the property profile of the products.

Suitable difunctional parent monomers —[$V^1$]— of the $V^1$ repeat units are, for example, the halocarboxylic esters of the polyalkylene oxide diols. Preferred starting materials for their synthesis are low molecular weight, oligomeric and polymeric alkylene oxides of the general composition

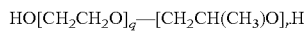

where q and r each have the definitions specified above, and the units are random or blocklike. Preferred representatives with regard to the alkylene oxide block are ethylene glycol, diethylene glycol, triethylene glycol, tetraethylene glycol, the oligoethylene glycols having molecular weights of from 200 to 10 000 g/mol, especially from 300 to 800 g/mol, and also 1,2-propylene glycol, 1,3-propylene glycol and dipropylene glycol.

The alkylene oxides are esterified in a manner known per se (Organikum, Organisch-chemisches Grundpraktikum [Basic Organic Chemistry Practicals], 17th edition, VEB Deutscher Verlag der Wissenschaften, Berlin 1988, p. 402-408) by reaction with the $C_2$ to $C_4$ halocarboxylic acids, their anhydrides or acid chlorides. Preference is given to using the acid chlorides of chloroacetic acid and 3-chloropropionic acid and to carrying out the reaction in the absence of solvents.

In an analogous manner, it is possible to convert alkanediols, alkenediols and alkyndiols to the corresponding reactive ester derivatives. Examples of alcohols are 1,4-butanediol, 1,6-hexanediol, 1,4-but(-2-)enol and 1,4-but(-2-)ynol.

Alkylene, alkenylene, alkynylene and aryl units are introduced preferably starting from the corresponding halides, especially chlorides and bromides. Examples of representatives are 1,6-dichlorohexane, 1,4-dichlorobut(-2-)ene, 1,4-dichlorobut-(-2-)yne and 1,4-bis(chloromethyl)benzene.

Polyalkylene oxide units may likewise be introduced via the α,ω-dihalogen compounds. These are obtainable from the oligomeric and polymeric alkylene oxides of the general composition

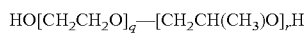

where q and r are each as defined above, for example by chlorination of the hydroxyl groups with $SOCl_2$ (Organikum, Organisch-chemisches Grundpraktikum, 17th edition, VEB Deutscher Verlag der Wissenschaften, Berlin 1988, p. 189-190). Mono-, di- or polyhydroxy-functional units as group $V^1$ may be introduced starting from epoxide derivatives.

Commercial examples are 1-chloro-2,3-epoxypropane, glycerol 1,3-bisglycidyl ether and diethylene glycol diglycidyl ether and neopentyl glycol diglycidyl ether.

When they are not commercially available, the desired diepoxides may be synthesized, for example, by reaction of the corresponding diols with 1-chloro-2,3-epoxypropane under alkaline conditions.

It lies within the scope of the invention to introduce siloxane chains $Z^1$ into the structure of $V^1$. This gives rise, inter alia, to the possibility of using siloxane chains of different length for the formation of the overall molecule. It is a preferred variant to incorporate into $V^1$ siloxane chains $Z^1$ of the chain length range $n_2=0$ to 19, preferably from 0 to 15, more preferably from 0 to 10, especially from 0 to 5, more especially 0. Suitable starting materials for the incorporation are, for example, the corresponding α,ω-diepoxides or α,ω-di(monohalocarboxylic acid) ester structures. In the case of the reaction of epoxides with primary or secondary amines, it should be noted that one mole of $H^+$ has to be added per mole of epoxide/tertiary amine for alkylations of tertiary amino groups.

The selection of suitable amines as starting components for the formation of Q in the $—[V^1—(Q—V^1)_x]—$ repeat unit likewise determines to a high degree the molecular structure. The use of ditertiary amines (corresponding to $—[N—N]—$, for example N,N,N',N'-tetramethylethylenediamine, N,N,N',N'-tetramethyltetramethylenediamine, N,N,N',N'-tetramethylhexamethylenediamine, N,N'-dimethylpiperazine, leads to products in which each nitrogen atom of the repeat unit is quaternized.

The use of secondary-tertiary diamines, for example N-methylpiperazine, opens up the route to repeat $—[V^1—(Q—V^1)_x]—$ units in which tertiary and quaternary amine and ammonium structures are present in a ratio of 1:1. A partial or complete subsequent quaternization of remaining tertiary amino structures constitutes a preferred variant for the establishment of a desired high density of the quaternary ammonium groups. The corresponding aromatic amines, imidazole and pyrazole, lead to products having a delocalized charge.

When primary-tertiary diamines, for example N,N-dimethylpropylenediamine and 1-(3-aminopropyl)imidazole, are used, especially in combination with diepoxides, it is possible to form comb-like structures for which the degree of quaternization during a final alkylation can be selected. In principle, the alkylations may also be adjusted to degrees of quaternization of, on average, less than one quaternary ammonium group per repeat $—[V^1—(Q—V^1)_x]—$ unit. However, preference is given to quaternizing at least one nitrogen atom per repeat unit.

Starting from disecondary amines, for example piperazine, N,N'-bis(2-hydroxyethyl)hexamethylenediamine, N,N'-bis(2-hydroxypropyl)hexamethylenediamine, it is also possible in principle to synthesize repeat $—[V^1—(Q—V^1)_x]—$ units with an average content of less than one quaternary ammonium group. In this case, the disecondary amines initially afford polytertiary amino-modified siloxane copolymers or else prepolymers which can subsequently be quaternized partly or fully to $—[V^1—(Q—V^1)_x]—$ in a final reaction. However, it is preferred in this variant too to quaternize at least one nitrogen atom per repeat unit.

Suitable quaternizing agents are the commonly known substance groups such as alkyl halides, halocarboxylic esters, epoxide derivatives in the presence of $H^+$ and dialkyl sulfates, especially dimethyl sulfate.

In a preferred embodiment, commercially unavailable disecondary amines are prepared starting from the corresponding diprimary amines, for example hexamethylenediamine, by alkylation with epoxides, for example ethylene oxide, propylene oxide, isopropyl glycidyl ether, utilizing the different reaction rates of primary and secondary amines.

It has already been stated that the possibility exists within the scope of the invention of introducing siloxane chains $Z^1$ into the structure of $V^1$. Suitable starting materials named by way of example have been the reactive intermediates α,ω-diepoxides and α,ω-di(monohalocarboxylic acid) esters.

Useful anions $A^-$ which neutralize the positive charges resulting from the ammonium groups may preferably be the ions formed during the quaternization, such as halide ions, especially chloride and bromide, alkylsulfates, especially methosulfate, carboxylates, especially acetate, propionate, octanoate, decanoate, dodecanoate, tetradecanoate, hexadecanoate, octadecanoate, oleate, sulfonates, especially toluenesulfonate. However, it is also possible to introduce other anions by ion exchange. Mention should be made, for example, of organic anions such as polyether carboxylates and polyether sulfates.

The quaternization reactions are performed preferably in water, polar organic solvents or mixtures of the two components mentioned. Suitable solvents are, for example, alcohols, especially methanol, ethanol, isopropanol and n-butanol, glycols such as ethylene glycol, diethylene glycol, triethylene glycol, the methyl, ethyl and butyl ethers of the glycols mentioned, 1,2-propylene glycol and 1,3-propylene glycol, ketones such as acetone and methyl ethyl ketone, esters such as ethyl acetate, butyl acetate and 2-ethylhexyl acetate, ethers such as tetrahydrofuran, and nitro compounds such as nitromethane. The selection of the solvent depends substantially on the solubility of the reaction partners, the desired reaction temperature and any reactivity present which disrupts the reaction.

The reactions are carried out in the range from 20° C. to 130° C., preferably from 40° C. to 100° C.

In order to prevent the formation of gel-like linear polyorganosiloxane polymers which are not fully soluble, an upper limit is appropriately placed on the molar mass.

A limit in the molecular weight is brought about by the end-capping resulting from the reaction between epoxides and any water or alcohol present in the reaction system, or alternatively by the additional use of tertiary amines such as trialkylamines or monofunctional compounds reactive toward amino groups.

In other words, the polyorganosiloxane polymers may, in addition to the terminal groups which result by their nature from the reaction of the monomeric starting materials, also have from monofunctional chain terminators such as trialkylamines etc. and, for example, ammonium, amino, ether or hydroxyl end groups resulting therefrom. All cases of end-capping are embraced by the aforementioned definition —Q—R and/or —V—R, where Q, V and R are each as defined above and R may be replaced by hydrogen.

The polysiloxanes of the general formula (I) used as component b1) in accordance with the invention may also contain branch units $V^3$. $V^3$ is a trivalent or higher-valency, straight-chain, cyclic or branched, saturated, unsaturated or aromatic hydrocarbon radical which has up to 1000 carbon atoms and may optionally contain one or more groups selected from —O—, —CONH—, —CONR$^2$— where $R^2$ is as defined above, —C(O)—, —C(S)—, —Z$^1$—, which is as defined above, —Z$^2$— which is as defined above and $Z^3$ where $Z^3$ is a trivalent or higher-valency organopolysiloxane unit. The branch unit $V^3$ may be silicone-free. Examples thereof include:

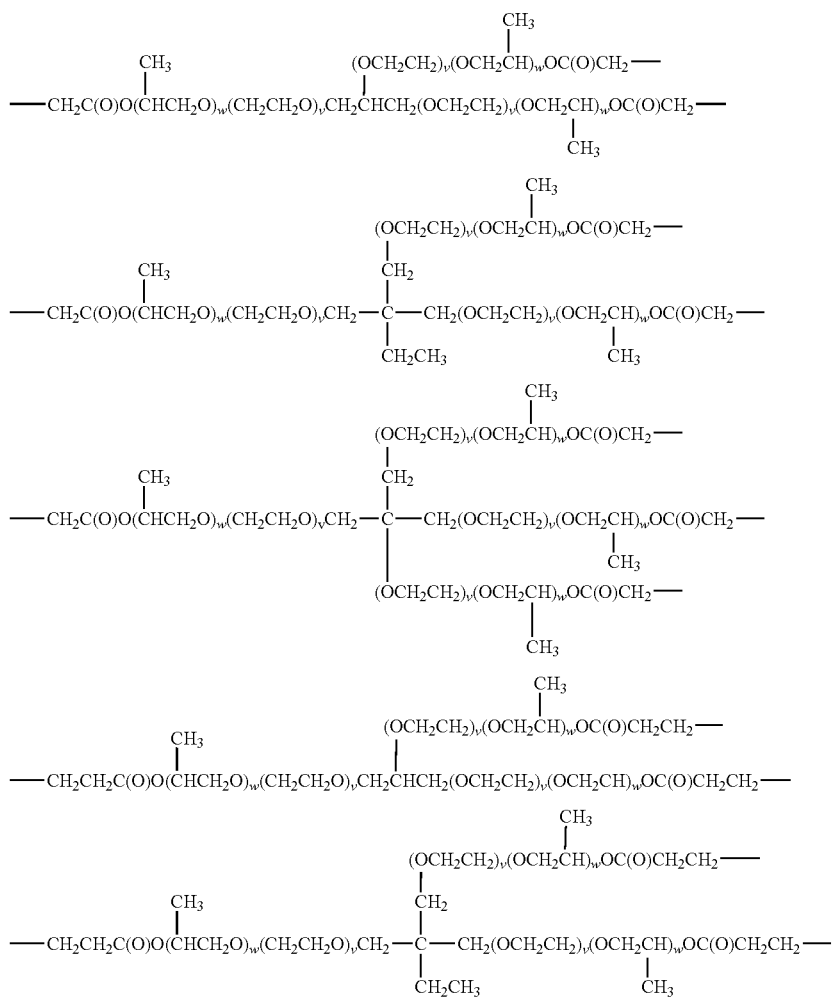

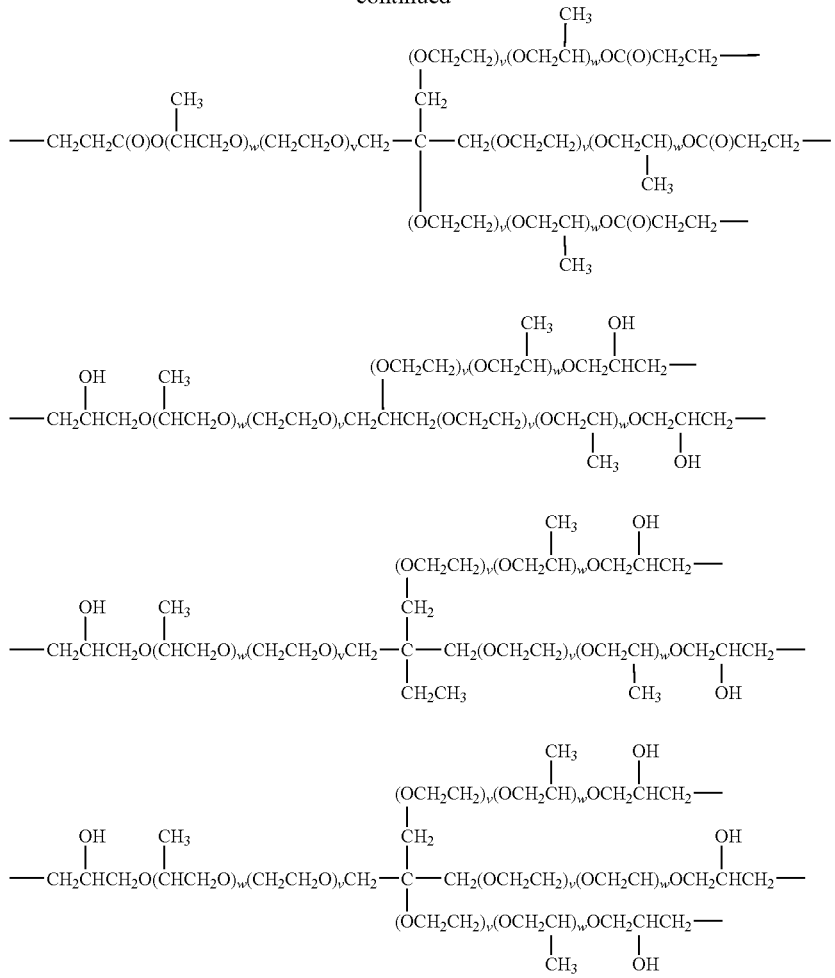
where v+w≧0.
The branch unit $V^3$ may be a trivalent or high-valency organopolysiloxane unit, for example:
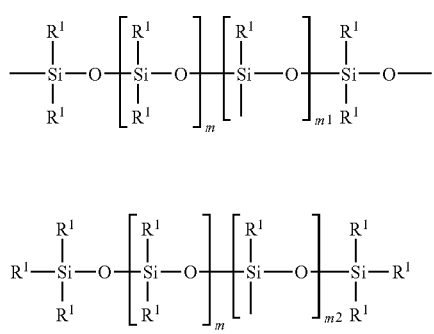
in which $R^1$ is as defined above, m=from 0 to 1000, and $m^1 \geqq 1$ and $m^2 \geqq 3$,
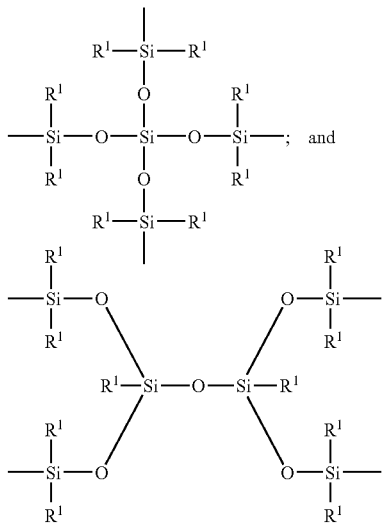
in which $R^1$ is in each case as defined above.
One example of a $Z^3$-containing branch unit $V^3$ is, for example:

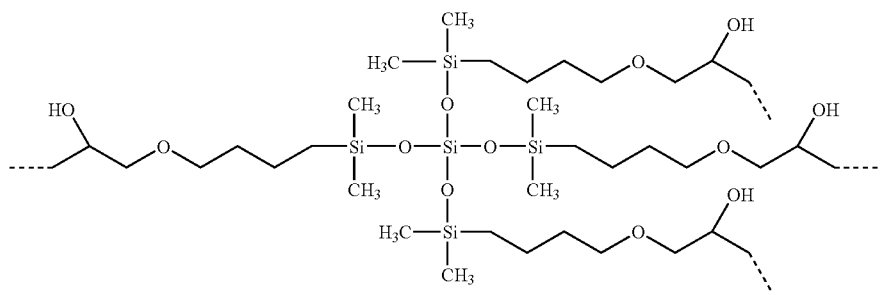

The polyamino- and/or polyammonium-polysiloxane compounds b1) used may be solid or liquid at 25° C. In the case that they are liquid at 25° C., the viscosities of the polysiloxanes b1) mentioned are preferably between 500 and 50 000 000 mPa·s at 25° C., preferably from 1000 to 2 500 000 mPa·s at 25° C., and at a shear rate gradient of D=1 s$^{-1}$. They may have melting points up to 250° C., but are water-soluble or -dispersible. Their solubility is preferably more than 1 g/l at 25° C.

The component b2) used may be one or more one amino- and/or ammonium-polysiloxane compounds b2). As explained above, these contain amino or ammonium groups only in the pendent groups. The amino- and/or ammonium- polysiloxane compounds b2) are preferably polysiloxanes which bear primary and/or secondary and/or tertiary amino groups in the pendent groups, in which the amino groups may optionally be protonated or quaternized, and which may optionally contain additional hydrophilic groups. The amino or ammonium groups mentioned are preferably bonded to the siloxane skeleton via carbon. The amino- and/or ammonium- polysiloxane compounds b2) mentioned are preferably poly- alkylsiloxanes having aminoalkyl- or aminoarylsiloxane units. The aminoalkyl units may be bonded to the difunc- tional, trifunctional or the monofunctional end groups, and be part of other oxygen-containing pendent groups, in particular of polyether pendent groups.

The additional hydrophilicizing groups optionally present are preferably those which derive from polyalkylene oxides and saccharides.

The aminopolysiloxanes mentioned are linear or branched polysiloxanes which are formed from siloxy units which are selected from the group consisting of:

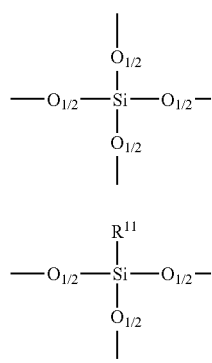

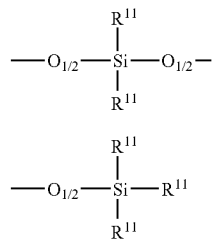

in which $R^{11}$ represents organic radicals which may be the same or different with the proviso that at least one of the $R^{11}$ radicals contains at least one nitrogen atom.

The $R^{11}$ substituents are preferably selected from the group consisting of:

straight-chain, cyclic or branched, saturated, unsaturated or aromatic hydrocarbon radical which has up to 200 carbon atoms and may optionally contain one or more groups selected from:

—O—,

—$NR^2$— where $R^2$ may be hydrogen, a monovalent, straight-chain, cyclic or branched, saturated, unsaturated or aromatic hydrocarbon radical which has up to 100 carbon atoms, may contain one or more groups selected from —O—, —NH—, —C(O)— and —C(S)—, and is optionally substituted by one or more substituents selected from the group consisting of a hydroxyl group, an optionally substituted hetero- cyclic group preferably containing one or more nitro- gen atoms, amino, alkylamino, dialkylamino, ammo- nium, polyether radicals and polyether ester radicals, where, when a plurality of —$NR^2$ groups is present, they may be the same or different,

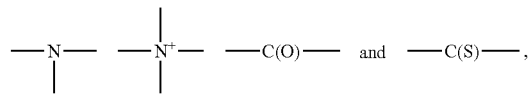

and the radical may optionally be substituted by one or more substituents selected from hydroxyl and

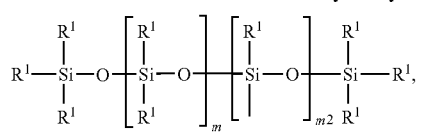

where $R^1$, m, m2 are each as defined above, hydroxyl, a polyether radical which has up to 20 000 carbon atoms and may optionally bear one or more amino, mono- or dialkylamino, or arylamino groups, a saccharide-containing organic radical, or two $R^{11}$ substituents from different siloxy units together form a straight-chain, branched or cyclic alkanediyl radical having from 2 to 12 carbon atoms between two silicon atoms, with the proviso that at least one $R^{11}$ substituent per molecule contains nitrogen, i.e., constitutes a nitrogen-containing $R^{11}$ radical.

$R^{11}$ is preferably alkyl, in particular methyl.

Preferred $R^{11}$ radicals which have nitrogen are, for example:

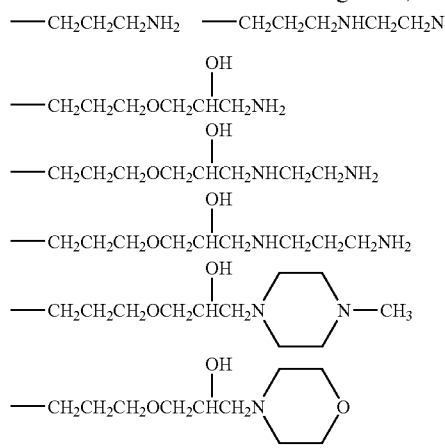

-continued

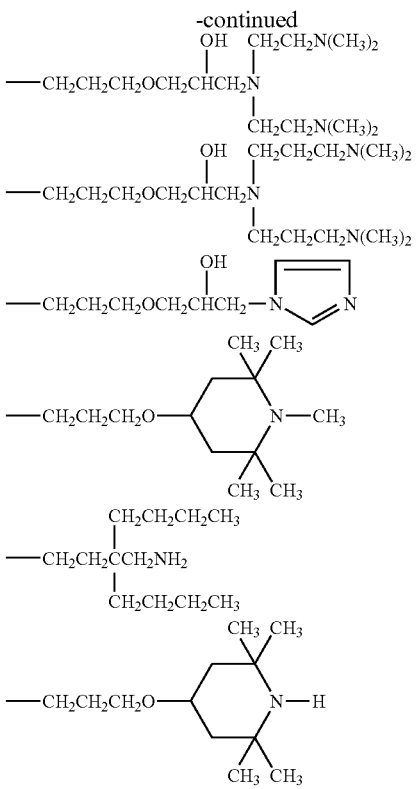

Further preferred amino- and ammonium-containing $R^{11}$ radicals are, for example:

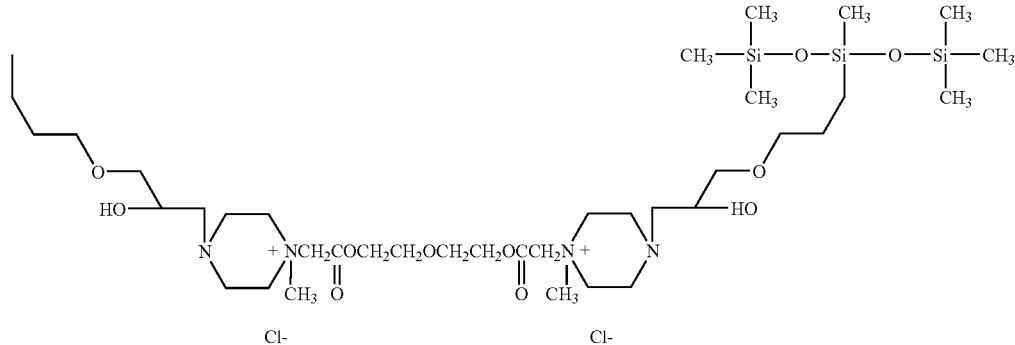

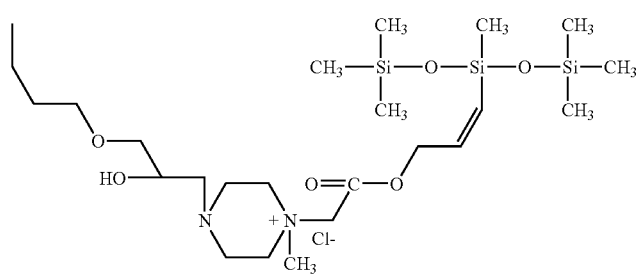

Corresponding aminopolysiloxanes having such $R^{11}$ radicals are disclosed in WO 02/10256, whose disclosure content belongs to the present application.

The nitrogen-containing $R^{11}$ radical is preferably aminopropyl or aminoethylaminopropyl. Further preferred nitrogen-containing $R^{11}$ radicals are formed from the reaction of glycidyloxypropylsiloxanes with mono- or dialkylamines. Preferred compounds as component b2) are therefore, for example, aminopolysiloxanes which arise from the reaction of epoxyalkylsiloxanes with ammonia, primary or secondary amines, such as those from the reaction of glycidyloxypropylsiloxanes with mono- or dialkylamines. Preferred alkoxy radicals for $R^{11}$ are methoxy, ethoxy, propoxy, isopropoxy, butoxy, hexyloxy and cyclohexyloxy.

Preferred polyether radicals which have up to 20 000 carbon atoms and may optionally bear one or more amino-, mono- or dialkylamino, or arylamino groups for $R^{11}$ include, for example:

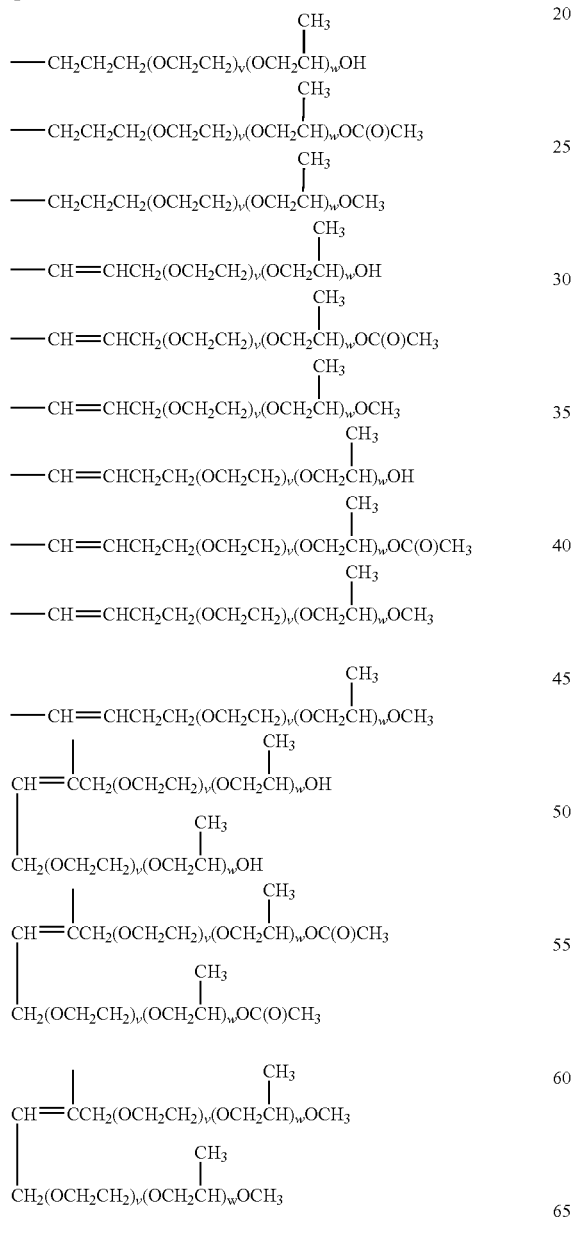

Saccharide-containing organic radicals for $R^{11}$ are, for example:

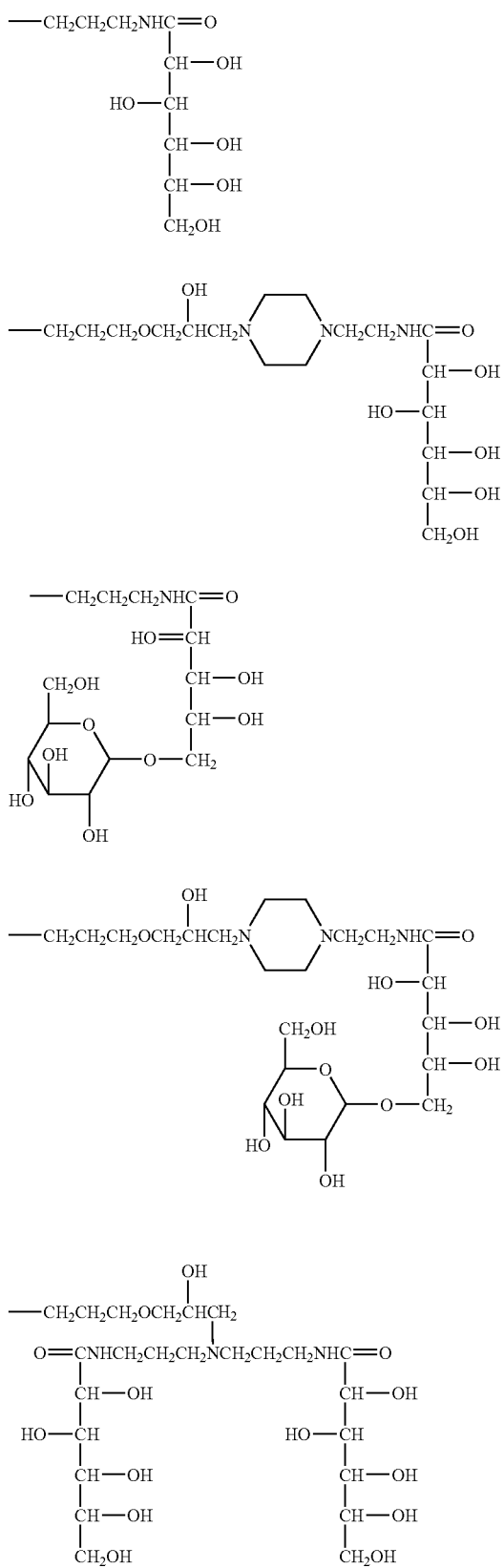

-continued

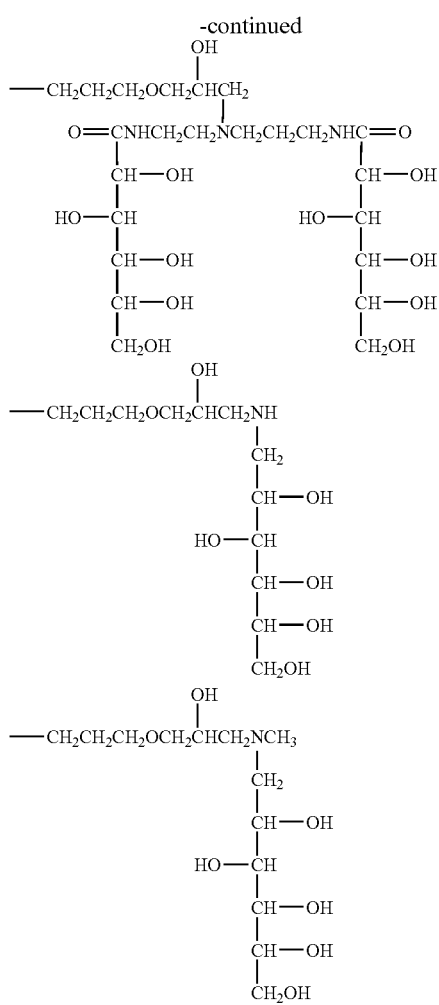

The preparation of such saccharide-containing polysiloxanes can be found, for example, in DE 4 318 536, DE 4 318 537.

The average degree of polymerization of the polysiloxane moiety of the aminopolysiloxanes b2) used in accordance with the invention, which results from Mn, is appropriately from 1 to 3000, preferably from 200 to 1000.

The ratio of the nitrogen-free polyorganosiloxane units to the nitrogen-containing polyorganosiloxane units in the aminopolysiloxanes b2) used in accordance with the invention is appropriately from 1:1 to 500:1.

The ratio of the polyether- or saccharide-containing polyorganosiloxane units to the remaining polyorganosiloxane units may be from 0 to 1.

The typical nitrogen content of the aminopolysiloxanes b2) used in accordance with the invention is, for example, between 0.005% by weight to 18% by weight, preferably from 0.02% by weight to 5% by weight, more preferably from 0.02% by weight to 1.5% by weight.

The aminopolysiloxanes b2) used may be solid or liquid at 25° C. In the case that they are liquid at 25° C., the viscosities of the aminopolysiloxanes b2) used in accordance with the invention are preferably between 500 to 500 000 mPa·s at 25° C., preferably from 1000 to 25 000 mPa·s at 25° C., and at a shear rate gradient of D=1 s$^{-1}$.

They may have melting points up to 250° C., but are water-soluble or -dispersible. Their solubility is preferably more than 1 g/l at 25° C.

Some of the above-described aminopolysiloxanes b2) used in accordance with the invention are obtainable, for example, as Wacker Finish® WR 1100 and General Electric® SF 1923.

The preferred amount of component b), i.e. b1)+b2), based on the total amount of the formulation, is from 1 to 30% by weight, preferably from 1 to 20% by weight.

The component c) used optionally is one or more silicone-free, preferably cationic, surfactants. It is preferably at least one constituent which is selected from nonpolymerized, organic, quaternary ammonium compounds. It preferably comprises hydrocarbon-containing quaternary ammonium salts or amine salts, and the hydrocarbon groups may preferably contain from 8 to 28 carbon atoms.

Examples of components c) are compounds of the following formula:

$$R^{12}R^{13}R^{14}R^{15}N^+X^-$$

in which $R^{12}$, $R^{13}$, $R^{14}$ and $R^{15}$ are each independently selected from the group consisting of: $C_1$-$C_{28}$-alkyl, alkenyl, hydroxyalkyl, benzyl, alkylbenzyl, alkenylbenzyl, benzylalkyl and benzylalkenyl, and X is an anion. The hydrocarbon groups $R^{12}$, $R^{13}$, $R^{14}$ and $R^{15}$ may independently be polyalkoxylated, preferably polyethoxylated or polypropoxylated, more preferably with groups of the general formula $(C_2H_4O)_yH$ where y=from 1 to 15, preferably from 2 to 5. Not more than one of the $R^{12}$, $R^{13}$, $R^{14}$ and $R^{15}$ groups should be benzyl. The $R^{12}$, $R^{13}$, $R^{14}$ and $R^{15}$ groups may each independently contain one or more, preferably two, ester (—[—O—C(O)—]; [—C(O)—O—]) and/or amido groups (—[CO—N($R^{12}$)—]; [—N($R^{12}$)—CO—]) in which $R^{12}$ is as defined above. The anion X may be selected from halides, methosulfate, acetate and phosphate, preferably from halides and methosulfate. Further examples of component c) are tetraorgano-substituted quaternary ammonium compounds having one or two long-chain C8 to C28 hydrocarbon radicals and two or three short-chain C1 to C6 hydrocarbon radicals. The long-chain radicals are preferably C12 to C20 chains and the short-chain radicals are preferably methyl, ethyl, propyl, butyl, hexyl, phenyl and hydroxyethyl, 2-hydroxypropyl. Preferred counterions are $Cl^-$, $Br^-$, $CH_3OSO_3^-$, $C_2H_5OSO_3^-$, $NO_3^-$, $HCOO^-$ and $CH_3COO^-$.

Examples include:

dodecylethyldimethylammonium bromide didodecyldimethylammonium bromide.

In the cationic surfactants which contain only one long-chain hydrocarbon group $R^{12}$, the chain length of the long-chain hydrocarbon group is preferably from 12 to 15 carbon atoms, and the short-chain radicals $R^{13}$, $R^{14}$ and $R^{15}$ are preferably methyl and hydroxyethyl.

In the cationic surfactants which contain two, three or even four long-chain hydrocarbon groups, the chain length of the long-chain hydrocarbon groups is preferably from 12 to 28 carbon atoms.

Preferred ester-containing surfactants have the formula:

$$\{(R^{16})_2N[(CH_2)_zER^{17}]_2\}^+X^-$$

in which $R^{16}$ is independently selected from $C_{1-4}$ alkyl, hydroxyalkyl or $C_{2-4}$ alkenyl; and in which $R^{17}$ is independently selected from $C_{8-28}$ alkyl or alkenyl groups; E is an ester group, i.e. —OC(O)— or —C(O)O—, z is an integer from 0 to 8 and $X^-$ is as defined above. They contain two or three short-chain C1 to C6 hydrocarbon radicals. The one or two long alkyl radicals per molecule derive from fatty acids of lengths from C8 to C26, preferably from C10 to C20, especially from C12 to C18. The fatty acids or the cuts of the chain length ranges mentioned may be saturated fatty acids, unsaturated fatty acids, hydroxy-substituted fatty acids or mixtures thereof. Examples of the acids mentioned are lauric acid, myristic acid, palmitic acid, stearic acid, oleic acid and ricinoleic acid. Further examples are tallow fatty acid and coconut fatty acid cuts. They are bonded to the quaternized nitrogen preferably via oxyethyl, 2-oxypropyl or 1,2-dioxypropyl or oligooxyethylene spacers. The short-chain radicals are preferably methyl, ethyl, propyl, butyl, hexyl, phenyl and hydroxyethyl, 2-hydroxypropyl. Preferred counterions are $Cl^-$, $Br^-$, $CH_3OSO_3^-$, $C_2H_5OSO_3^-$, $NO_3^-$, $HCOO^-$ and $CH_3COO^-$.

Examples include (tallow fatty acid oxyethyl)trimethylammonium methosulfate (coconut fatty acid pentaethoxy)trimethylammonium methosulfate di(tallow fatty acid oxyethyl)dimethylammonium chloride di(tallow fatty acid oxyethyl)hydroxyethylmethylammonium methosulfate di(tallow fatty acid 2-oxypropyl)dimethylammonium methosulfate 1,2-(ditallow fatty acid)oxy-3-trimethylpropaneammonium chloride A further type of preferred ester-containing cationic surfactants can be represented by the following formula:

$\{(R^{16})_3N(CH_2)_zCH[O(O)CHR^{17}][CH_2O(O)CR^{17}]\}^+X^-$, in which $R^{16}$, $R^{17}$, X, and z are each as defined above.

A further group of cationic surfactants c) is those of the formula $R^{18}A(CH_2)_{2\text{-}4}NR^{19}R^{20}$ in which $R^{18}$ is $C_6$-$C_{12}$ alkyl; A is a divalent group which is selected from —NH—, —CONH—, —COO— or —O—, or A may be absent. $R^{19}$ and $R^{20}$ are each independently selected from the group consisting of H, $C_1$-$C_{14}$ alkyl or $(CH_2—CH_2—O(R^{21}))$ in which $R^{21}$ is H or methyl.

Particularly preferred surfactants of this type are decylamine, dodecylamine, $C_8$-$C_{12}$ bis(hydroxyethyl)amine, $C_8$-$C_{12}$ bis(hydroxypropyl)amine, $C_8$-$C_{12}$ amidopropyldimethylamine or salts thereof.

Further surfactants include: fatty acid amides of the formula $R^{22}C(O)N(R^{23})_2$ wherein $R^{22}$ is an alkyl group having from 8 to 28 carbon atoms and $R^{23}$ is in each case a short-chain radical, preferably selected from hydrogen, $C_1$-$C_6$ alkyl and hydroxyalkyl. It is also possible to use $C_8$-$C_{28}$ N-alkylpolyhydroxy fatty acid amides. Typical examples include: $C_{12}$-$C_{18}$ N-methylglucamides (see WO 92/06154). Other sugar derivatives include, for example, $C_8$-$C_{28}$ N-(3-methoxy-propyl)glucamide. These likewise have two or three short-chain $C_1$ to $C_6$ hydrocarbon radicals. The one or two long alkyl radicals per molecule derive from fatty acids of lengths $C_8$ to $C_{26}$, preferably $C_{10}$ to $C_{20}$, especially $C_{12}$ to $C_{18}$. The fatty acids or the cuts of the chain length ranges mentioned may likewise be saturated fatty acids, unsaturated fatty acids, hydroxy-substituted fatty acids or mixtures thereof. Examples of the acids mentioned are lauric acid, myristic acid, palmitic acid, stearic acid, oleic acid and ricinoleic acid. Further examples are tallow fatty acid and coconut fatty acid cuts. They are bonded to the quaternized nitrogen preferably via amidoethyl and 3-amidopropyl spacers. The short-chain radicals are preferably methyl, ethyl, propyl, butyl, hexyl, phenyl and hydroxyethyl, 2-hydroxypropyl. They may also alternatively be cyclic radicals such as imidazolinium radicals into which fatty alkyl substituents have optionally additionally been incorporated. Preferred counterions are $Cl^-$, $Br^-$, $CH_3OSO_3^-$, $C_2H_5OSO_3^-$, $NO_3^-$, $HCOO^-$ and $CH_3COO^-$.

Examples include (undecylenic acid amidopropyl)trimethylammonium methosulfate (ricinoleic acid amidopropyl)trimethylammonium methosulfate 1-methyl-1-(tallow fatty acid amidoethyl)-2-(tallow fatty alkyl)imidazolinium methosulfate 1-methyl-1-oleylamidoethyl-2-oleylimidazolinium methosulfate 1,1-ethylenebis(1-methyl-2-(tallow fatty alkyl)imidazolinium) methosulfate.

In addition to the quaternary ammonium compounds, amine salts may also find use. These are salts of primary, secondary or tertiary amines with inorganic or organic acids.

In these amine salts, the nitrogen is substituted by one or two long-chain $C_8$ to $C_{28}$ hydrocarbon radicals, one to three hydrogen atoms and optionally one or two short-chain $C_1$ to $C_6$ hydrocarbon radicals. The one or two long alkyl radicals per molecule derive, for example, from fatty amines or fatty acids of lengths C8 to C26, preferably C10 to C20, especially C12 to C18. Preferred counterions are $Cl^-$, $Br^-$, $CH_3OSO_3^-$, $C_2H_5OSO_3^-$, $NO_3^-$, $HCOO^-$ and $CH_3COO^-$.

To increase the hydrophilicity, the fatty amines used may be ethoxylated. One example is the ethoxylated stearylamine derivative $CH_3(CH_2)_{17}N^+H[(CH_2CH_2O)_5H]_2$ $Cl^-$.

The fatty acids or the cuts of the chain length ranges mentioned may be the saturated fatty acids, unsaturated fatty acids, hydroxy-substituted fatty acids or mixtures thereof, which have already been described. Examples of the acids mentioned are lauric acid, myristic acid, palmitic acid, stearic acid, oleic acid and ricinoleic acid. Further examples are tallow fatty acid and coconut fatty acid cuts. They are bonded to the amine salt nitrogen preferably via oxyethyl, 2-oxypropyl, 1,2-dioxypropyl spacers in the case of esters, and preferably via amidoethyl and 3-amidopropyl spacers in the case of amides. The short-chain radicals are preferably methyl, ethyl, propyl, butyl, hexyl, phenyl and hydroxyethyl, 2-hydroxypropyl. Preferred counterions are $Cl^-$, $Br^-$, $CH_3OSO_3^-$, $C_2H_5OSO_3^-$, $NO_3^-$, $HCOO^-$ and $CH_3COO^-$.

Examples include stearic acid triethanolamine derivative:

$CH_3(CH_2)_{16}C(O)OCH_2CH_2N^+(CH_2CHOH)_2$ $Cl^-$ stearamide derivative $CH_3(CH_2)_{16}CONHCH_2CH_2N^+H_2CH_2CH_2N^+H_3$ $2Cl^-$ stearamide derivative $CH_3(CH_2)_{16}CONHCH_2CH_2N^+H_2CH_2CH_2OH$ $Cl^-$ palmitamide derivative $CH_3(CH_2)_{14}CONHCH_2CH_2N^+H(CH_3)_2$ $Cl^-$.

The amount of the optionally used component c), based on the total amount of the formulation, is from 0 to 30% by weight, preferably from 0 to 10% by weight. If component c) is present in the formulation, the amount is preferably between 0.01% by weight and 15% by weight, more preferably from 1 to 10% by weight.

Component c) in the inventive formulations has the function of improving the emulsifiability of component a) and in some cases of increasing the substantivity.

The optionally used coacervate formation agents as per component d) are appropriately cationic copolymers which are based on natural or synthetic polymer structures. They differ in this respect from the silicone-free cationic surfactants of component c) which are not based on polymer structures. Combinations of natural and synthetic polymers are likewise possible. Coacervate formation agents means complex charged anions or cations which each form a complex salt with changed dissolution behavior with a polymer or colloid particle charged in the opposite sense.

The term "coacervate phase" as used in accordance with the invention embraces all types of discontinuous phases, as described, for example, in "B. Jonsson, B. Lindman, K. Holmberg & B. Kronberb, "Surfactants and Polymers In Aqueous Solution", John Wiley & Sons, 1998" and in "L. Piculell & B. Lindman, Adv. Colloid Interface Sci., 41 (1992)". The mechanism of the coacervation and its specific influences are described, for example, in "Interfacial Forces in Aqueous Media", C. J. van Oss, Marcel Dekker, 1994, page 245 to 271. The term "coacervate phase" is occasionally also referred to in the literature as "complex coacervate phase" or as "associated phase separation".

The coacervate phase formation agent as per component d), optionally present in the invention formulation, leads, for example in the event that it comes into contact with anionic surfactants or anionic groups of any other components, for example in the application of the inventive formulation, such as in laundry detergent formulations, fiber treatment formulations or in the treatment of pretreated substrate surface (anionic assistants or soil particles), to the formation of coacervate phases.

This phase formation is visible, for example, microscopically using dyes.

For the substances as per d), the term "cationic" generally relates to protonated amino compounds or else quaternary ammonium compounds (tetraorganoammonium compounds).

Natural copolymers derive preferably from cellulose, starch or chitosan. As particularly advantageous natural copolymers, emphasis should be given to the guar gum derivatives modified by quaternary ammonium groups. These are commercially available as the Jaguar types from Rhône-Poulenc (Rhodia).

Synthetic copolymers are based preferably on cationic structures such as polyvinylamines, polyethyleneimines and polydimethyldiallylammonium halides. Alternatively, it is possible to use cationically modified materials based, for example, on polyvinylpyrrolidone, polyacrylamide, polymethylacrylamide, polyvinylimidazole and aminoalkylimidazole copolymers.

Particularly advantageous within this group are high molecular weight poly(vinylamine-vinylformamide) copolymers and high molecular weight polyethyleneimines.

Generally, high molecular weight natural or synthetic coacervate formation agents are to be preferred over low molecular weight structurally analogous compounds.

A third material group is that of complexes of polycationic and polyanionic compounds, i.e. complex salts.

Preference is given in this context to combinations of natural polymers and synthetic polymers. Specifically, they are combinations of anionic natural polymers with cationic synthetic polymers. The pairing of cationic natural polymer with anionic synthetic polymer is likewise possible. Examples of preferred combinations are carboxymethylcellulose/polyethyleneimine, carboxymethyl-cellulose/polyvinylamine, chitosan/polystyrenesulfonic acid, chitosan/polyacrylic acid, chitosan/polymethacrylic acid.

Preference is further given to combinations of two oppositely charged natural polymers or synthetic polymers. Examples thereof are the carboxymethyl-cellulose/chitosan, polyethyleneimine/polyacrylic acid and polyvinylamine/polystyrenesulfonic acid combinations.

The polycationic compounds may be used in the form of the bases or salts of monovalent anions. The polyanionic compounds may be used in the form of the acids or salts of monovalent cations.

Synthetic polycationic and polyanionic compounds may be used in the form of their copolymers, which allows their charge density to be adjusted variably.

When the complexes considered above are used, it has to be ensured that their net charge is cationic. This means that, irrespective of the specific pairing, an excess of amino or ammonium groups relative to the anionic groups such as carboxylic acid, sulfonic acid, sulfuric monoesters and salts thereof is present.

As a result of the complexation of polycationic with polyanionic compounds of the above-described type, the molar mass of the coacervate formation agent rises in a desired manner.

If the coacervate formation agent d) is present in the inventive formulation, its preferred amount is from 0.001 to 5% by weight, more preferably from 0.1 to 1% by weight, based on the total amount of the formulation.

The component e) used in the inventive formulation comprises one or more carrier substances. These are selected preferably from solid carrier substances f) and/or liquid carrier substances g). In the context of the present invention, this means that the liquid carriers are liquid at 40° C., and the solid carriers are solid at 40° C.

Preferred liquid carriers g) include aqueous and nonaqueous carriers and may include: water alone or organic solvents, preferably water-soluble organic solvents alone and/or mixtures thereof with water. Preferred organic solvents include: monoalcohols, diols, polyols such as glycerol, glycol, polyethers such as polyalkylene glycols such as polyethylene glycols and mixtures thereof, also with water. Particular preference is given to mixtures of solvents, in particular mixtures of lower aliphatic alcohols such as ethanol, propanol, butanol, isopropanol and/or diols such as 1,2-propanediol or 1,3-propanediol; or mixtures thereof with glycerol. Suitable alcohols include in particular $C_1$-$C_4$ alcohols. Preference is given to 1,2-propanediol.

The liquid carrier g) is appropriately present in the inventive formulation, based on the total amount of the formulation, in an amount of from 0 to 95% by weight, preferably from 0 to 65% by weight, more preferably from 0 to 55% by weight. When the liquid carrier g) is present in the inventive formulation, its preferred amount is more than 5% by weight, more preferably more than 10% by weight, most preferably from more than 30 to 70% by weight, more preferably to 60% by weight.

The solid carrier f) used as component e) is preferably selected from compounds which are solid at 40° C. They are more preferably compounds which are selected from the group of the water-soluble compounds which have a solubility in water of at least 100 grams/liter at 20° C. Examples of the solid carriers include:

Inorganic or organic salts, polyhydroxy compounds, saccharides, amides such as urea, and relatively high molecular weight polyethylene oxides. The solid carriers f) are preferably compounds which have no significant interface-active action in the sense of surfactants. Examples of inorganic salts are sodium chloride, potassium chloride, sodium carbonate, sodium sulfate. An example of an organic salt is sodium acetate. Examples of polyhydroxy compounds and saccharides which can be used in accordance with the invention are pentaerythritol, sorbitol, glucamine, N-methylglucamine. Amide derivatives which can be used in accordance with the invention are, for example, urea and strongly hydrophilic, saccharide-modified amide derivatives such as ethylenediaminebisgluconamide, 1,3-propylenediaminebisgluconamide, 1,2-propylenediaminebisgluconamide, diethylenetriaminebisgluconamide, dipropylenetriaminebisgluconamide, N-methyldipropylenetriaminebisgluconamide, N,N-dimethylethylenediaminegluconamide, N,N-dimethylpropylenediaminegluconamide. The latter saccharide-modified derivatives are obtainable by regioselective reaction of the primary amino groups of the corresponding amines with saccharide-carboxylic acid lactones such as gluconolactone or glucopyranosylarabinolactone (DE 4 318 536, DE 4 318 537).

The solid carrier f) is appropriately present in the inventive formulation, based on the total amount of the formulation, in an amount of from 0 to 95% by weight, preferably from 0 to 65% by weight, more preferably from 0 to 55% by weight. When the solid carrier f) is present in the inventive formulation, its preferred amount is more than 5% by weight, more preferably more than 10% by weight, most preferably from more than 30 to 70% by weight, more preferably to 60% by weight.

The solid carrier f) and the liquid carrier g) may be present in any ratios relative to one another. The selection of the ratio depends upon whether liquid, pasty or solid compositions of the formulation are desired.

Depending on the fields of use, the inventive formulation may comprise further other ingredients or assistants in addition to the above-described components a) to g).

In the case of use in laundry detergents, for example, what are known as builders, for example zeolites, silicates, polyphosphates, alkali metal citrates, alkali metal 2,2-oxydisuccinates, alkali metal carboxymethyloxysuccinates, alkali metal nitrilotriacetates and sodium carbonate, enzymes, defoamers such as silicone compounds and stabilizers may be present. The stabilizers serve, for example, to stabilize the component b) by preventing its coagulation and sedimentation. The stabilizers are, for example, gums and other polysaccharides, for example carrageenan gum, other thickeners or rheology additives. The stabilizer is preferably a crystalline hydroxyl-containing compound such as trihydroxystearin, a hydrogenated oil or a derivative thereof.

Further assistants which may be present in particular in laundry detergents are coupling agents such as hexylamine, octylamine, nonylamine, their C1-C3 secondary or tertiary analogs, and alkanediols.

Further assistants which may be present in laundry detergents in particular are fragrances which adhere to the substrates, chelating agents, other surface-active substances.

The preparation of the inventive formulation may include, for example, the preparation of a homogeneous base mixture a)+b) and the introduction of the optional components c) to e).

In an advantageous embodiment of the invention, the components a) and b) are initially mixed homogeneously to give a premixture, optionally with addition of parts of the carrier substance e). In the context of the invention, homogeneous means substantially dissolved or else transparently finely dispersed. The optional component c), for example, may subsequently be introduced into this homogeneous premixture. Depending on the structure of the premixture components a) and b) and of the component c) this introduction may lead in turn to a homogeneous mixture or else to a visibly more coarsely disperse distribution of c) in the a)+b) premixture. Depending on the end application, d), (optionally further) e), i.e. f) and/or g), may be introduced into this mixture.

In a further preferred embodiment of the invention, a solution of c) in water e) or a solution of d) in water e) or a mixture of c) and d) is introduced into the a)+b) premixture. An addition of c)+d)+e) to the a)+b) premixture likewise lies within the scope of the invention.

It is possible using these different mixing strategies to influence the microscopic distribution of the components in the overall system and thus the product properties.

The invention further relates to the use of the inventive formulation in cosmetic formulations, in laundry detergents or for the surface treatment of substrates.

The invention further relates to the use of the inventive formulation for fiber treatment or fiber finishing.

The invention further relates to the use of the inventive formulation for the treatment of textiles and other natural and synthetic fiberlike materials including paper.

The inventive formulations are particularly suitable for use in the presence of anionic surfactants, in particular in laundry detergent formulations or in the treatment of pretreated fibers.

The invention further relates to the use of the inventive formulation as a softener.

The above-described mixtures constitute formulations which are suitable for the treatment of textiles and other natural and synthetic fiberlike materials, especially in the presence of anionic surfactants from laundry detergent formulations or compositions for fiber pretreatment. For this purpose, the inventive formulations may be incorporated directly into laundry detergents or else metered separately into the running washing process. As a result of the use of the inventive formulations during the washing process, a silicone-typical softness, improved elasticity and reduced creasing tendency are imparted to the treated substrates.

In addition, the formulations described may find use as a constituent of separate softener systems after the washing of fibers and textiles. In addition, the formulations described may find use for the surface treatment of substrates such as natural and synthetic fibers, including paper and textiles, as a constituent of systems for initial textile finishing, as an ironing aid and composition for the prevention and reversal of textile creases. It is also possible to introduce the inventive formulation into cosmetic systems for the treatment of hair and skin.

The inventive formulations may be present in liquid, including pasty, or solid form. In addition, the formulation may be present in encapsulated form or in a liquid or solid matrix.

A preferred formulation of the present invention contains:

a): from 5 to 99, preferably from 10 to 80, more preferably from 10 to 40, b): from 1 to 95, preferably from 1 to 30, more preferably from 1 to 20, c): from 0 to 10, preferably from 1 to 10, d): from 0 to 1, preferably from 0.1 to 1, e): from 0 to 70, preferably from 30 to 70, the data being percentages by weight based on the total weight of the formulation.

EXAMPLES

Example 1

Preparation of the Quat According to WO 02/10259

A 1 liter three-neck flask is initially charged at room temperature with 24 g of water and 4.18 g (0.048 mol of tertiary amino groups) of N,N,N',N'-tetramethyl-1,6-hexanediamine and 3.8 g (0.012 mol of primary amino groups) of an alkylene oxide derivative, obtainable under the trade name Jeffamine® ED 600, of the structure

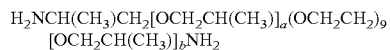

where $a+b=3.6$.

Within 5 minutes, 12.0 g (0.03 mol) of dodecanoic acid in the form of a 50% solution in 2-propanol and 1.8 g (0.03 mol) of acetic acid are added. After the mixture has been heated to 50° C., 194.1 g (0.06 mol of epoxy groups) of an epoxysilane of the average composition

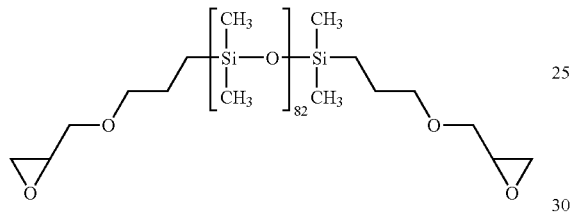

and 30 ml of 2-propanol are added dropwise within 30 minutes. The yellow, opaque mixture is heated to reflux temperature for 6 hours. After all constituents which are volatile up to 100° C./2 mmHg under reduced pressure have been removed, 204 g of a colorless, opaque material are obtained as component b1), which contains the following structural elements:

In the above formula, the Q, $V^1$ and $V^2$ repeat units are also included for the purposes of illustration. The molar ratio of the $V^1$-containing polysiloxane-free diamino components and the $V^2$-containing long-chain polysiloxane-containing diepoxy components of 1:1 results in a ratio of $V^2/V^1$ of 1:1.

Example 2

Preparation of the Quat According to WO 02/10257 a) 211.1 g (0.15 mol of epoxy groups) of an epoxysilane of the average composition

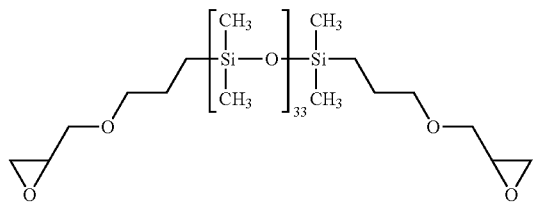

and 15.2 g (0.15 mol) of N-methylpiperazine are dissolved in 225 ml of isopropanol and heated to 90° C. for 4 hours. After the end of the reaction, the solvent was removed by distillation in a water-jet vacuum and finally in an oil-pump vacuum. 217 g of a clear, yellowish product of the structure

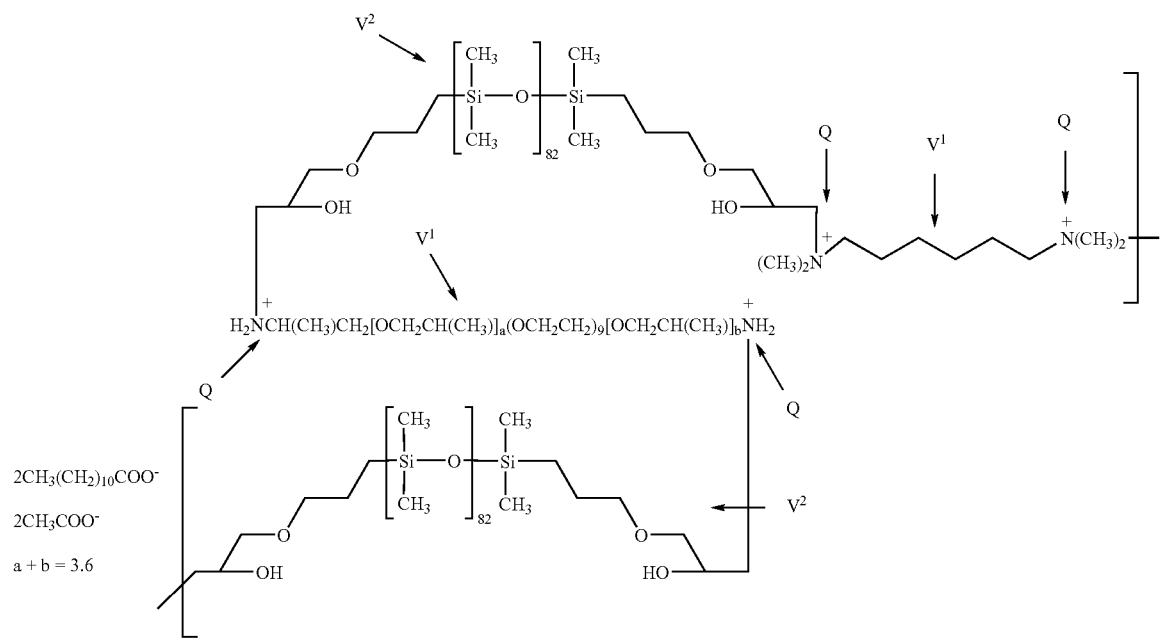

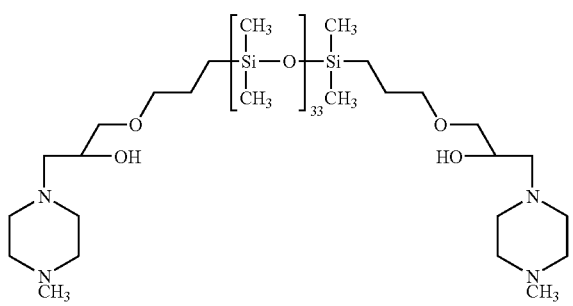

were obtained.

¹³C NMR:

| Substructure | shift (ppm) |
| --- | --- |
| ClCH₂ | 40.8 |
| ClCH₂—C(O)— | 167.3 |
| ClCH₂—CH₂—C(O)—OCH₂— | 65.2 |
| ClCH₂—CH₂—C(O)—OCH₂—CH₂— | 68.7 |
| —CH₂—OCH₃ | 58.8 | c) 19.61 g (6.5×10⁻³ mol) of the α,ω-aminosiloxane as per example 4a) and 3.12 g (1.3×10⁻² mol) of the chloroacetic ester as per example 4b) were dissolved in 50 ml of isopropanol under nitrogen and heated to reflux temperature for 12 hours. After the reaction had ended, all constituents which boiled up to 70° C. and at 20 hPa were removed. 19.7 g of a yellowish-light brown viscous oil of the formula:

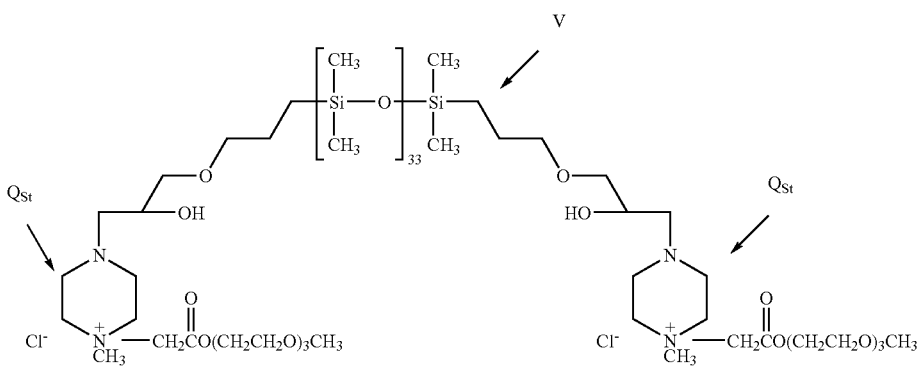

were obtained as component b1). Gas chromatography detected a quantitative conversion of the ester.

¹³C NMR:

¹³C NMR:

| Substructure | shift (ppm) |
| --- | --- |
| —CH(OH)— | 66.07 |
| —CH(OH)—CH₂—N— | 60.74 |
| —CH(OH)—CH₂—N—CH₂— | 53.20 |
| —CH(OH)—CH₂—N—CH₂—CH₂— | 55.10 |
| CH₃—N≡ | 45.87 | b) 200 g (1.21 mol) of triethylene glycol monomethyl ether were initially charged at room temperature, 20° C., under nitrogen. With vigorous stirring, 151 g (1.34 mol) of chloroacetyl chloride were added dropwise within 30 minutes. During the dropwise addition, the temperature rose to 90° C. and intensive HCl evolution set in. On completion of the dropwise addition, the mixture was heated to 130° C. for 30 minutes. Subsequently, all constituents which boiled up to 130° C. and at 20 hPa were distilled off. 301 g of a light yellow, viscous liquid of the composition

were obtained.

The purity of the ester, determined by gas chromatography, was 99%.

| Substructure | shift (ppm) |
| --- | --- |
| —CH(OH)— | 65.9/66.1 |
| —CH(OH)—CH₂—N— | 52.6 |
| —CH(OH)—CH₂—N—CH₂— | 45.4 |
| —CH(OH)—CH₂—N—CH₂—CH₂— | 60.5/60.6 |
| —CH(OH)—CH₂—N—CH₂—CH₂—N⁺—CH₂— | 61.4 |
| —CH(OH)—CH₂—N—CH₂—N⁺—CH₂—C(O)— | 169.6/169.9 |
| CH₃—N⁺≡ | 52.9 |
| —CH₂—OCH₃ | 58.6 |

According to the ¹³C NMR spectrum, the quaternization proceeded selectively on the methyl-substituted nitrogen atoms.

Example 3

153 g (1.5 mol) of H₂NCH₂CH₂CH₂N(CH₃)₂ are initially charged under nitrogen in a four-neck flask. Within 15 minutes, 412.3 g (1.5 mol) of palmitoyl chloride are added dropwise. The addition is regulated in such a way that the mixture remains in the temperature range from 100° C. to 120° C. After the addition has been completed, vacuum is applied briefly in order to degas the white-yellowish viscous mass which has formed. 123 g (1.5 mol) of sodium acetate are added to this viscous mass at 100° C. After cooling, 556 g of a white-yellowish hard mass are obtained.

Composition:

Example 4

Starting from tetrameric cyclodimethylsiloxane or a cyclosiloxanepolydimethylsiloxanediol mixture and aminopropylmethyldiethoxysilane, aminopropyldimethylethoxysilane, optionally addition of water traces and hexamethyldisiloxane, known alkali-catalyzed equilibration and condensation with elimination of ethanol provides an aminosiloxane b2) of the following average relative formula:

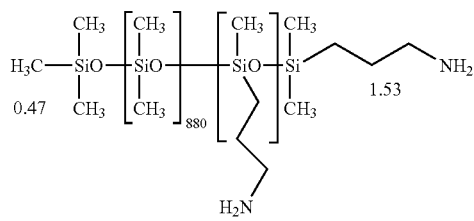

According to the $^1$H NMR spectrum, this material still contains traces of ethoxy groups.

Example 5

The following formulations are prepared:

| Formulation 1 | Formulation 2 |
|---|---|
| 14.5 g of siloxane quat as per example 1 | 14.5 g of aminosiloxane as per example 4 |
| 3.3 g of siloxane quat as per example 2 | 3.3 g of siloxane quat as per example 2 |
| 28.9 g of polydimethylsiloxane viscosity 1 000 000 mPa · s | 28.9 g of polydimethylsiloxane viscosity 1 000 000 mPa · s |
| 3.3 g of amine salt as per example 3 | 3.3 g of amine salt as per example 3 |
| 50 g of water | 50 g of water |

| Formulation 3 | Formulation 4 |
|---|---|
| 14.5 g of siloxane quat as per example 1 | 14.5 g of aminosiloxane as per example 4 |
| 3.3 g of siloxane quat as per example 2 | 3.3 g of siloxane quat as per example 2 |
| 28.9 g of polydimethylsiloxane viscosity 1 000 000 mPa · s | 28.9 g of polydimethylsiloxane viscosity 1 000 000 mPa · s |
| 3.3 g of amine salt as per example 3 | 3.3 g of amine salt as per example 3 |
| 50 g of water + 0.74 g of a cationic guar gum (MW 425 000; 0.7 mmol/g of N$^+$) | 50 g of water + 0.74 g of a cationic guar gum (MW 425 000; 0.7 mmol/g of N$^+$) |

To prepare the formulations, the two silicone quats for F1 or the aminosiloxane and the silicone quat for F2 are initially mixed with one another. The polydimethylsiloxane is stirred homogeneously into these mixtures. Subsequently, the amine salt is finely distributed in these premixtures. An opaque mass is formed in each case. Finally, the water is stirred slowly into F1 and F2, so that white emulsion-like liquids are obtained.

The aqueous guar gum solution is finally stirred into the formulations F3 and F4.

Example 6

To demonstrate the softening properties, wash experiments are carried out in a drum washing machine with a pulverulent (Dash® 2in1) laundry detergent and a liquid (Ariel Liquid®) laundry detergent.

| Wash experiment W1 |
|---|
| 40° C., 20 min, then 5× rinse |
| 110 g of Dash ® 2in1 matrix without bentonite |
| 2 kg of washing (1850 g of ballast material + 5 terry swatches, 150 g in total) |
| 10 l of water in the machine |
| 13.5 g of formulation F1 introduced separately directly after Dash 2in1 matrix |

| Wash experiment W2 | Wash experiment W3 |
|---|---|
| 40° C., 20 min, then 5× rinse | 40° C., 20 min, then 5× rinse |
| 110 g of Dash ® 2in1 matrix without bentonite | 75 g of Ariel liquid |
| 2 kg of washing (1850 g of ballast material + 5 terry swatches, 150 g in total) | 2 kg of washing (1850 g of ballast material + 5 terry swatches, 150 g in total) |
| 10 l of water in the machine | 10 l of water in the machine |
| 13.5 g of formulation F2 introduced separately directly after Dash 2in1 matrix | 13.5 g of formulation F2 introduced before the wash experiment in Ariel liquid |

| Wash experiment W4 | Wash experiment W5 |
|---|---|
| 40° C., 20 min, then 5× rinse | 40° C., 20 min, then 5× rinse |
| 110 g of Dash ® 2in1 matrix without bentonite | 75 g of Ariel liquid |
| 2 kg of washing (1850 g of ballast material + 5 terry swatches, 150 g in total) | 2 kg of washing (1850 g of ballast material + 5 terry swatches, 150 g in total) |
| 10 l of water in the machine | 10 l of water in the machine |
| 13.5 g of formulation F3 introduced separately directly after Dash 2in1 matrix | 13.5 g of formulation F4 introduced before the wash experiment in Ariel liquid |

The 5 terry swatches softened by F1 in wash experiment W1 were compared with 5 swatches which had been washed identically with 'Ariel® liquid' alone.

The 5 terry swatches softened by F2 in wash experiment W2 were compared with 5 swatches which had been washed identically with Ariel liquid alone.

The 5 terry swatches softened by F2 in wash experiment W3 were compared with 5 swatches which had been washed identically with Ariel liquid alone.

The 5 terry swatches softened by F3 in wash experiment W4 were compared with 5 swatches which had been washed identically with Ariel liquid alone.

The 5 terry swatches softened by F4 in wash experiment W5 were compared with 5 swatches which had been washed identically with Ariel liquid alone.

On a scale from 0 to 4 points, i.e. 1=very good, the swatches washed in accordance with the invention achieved the following scores:

| | Experiment | | | | |
|---|---|---|---|---|---|
| | W1 | W2 | W3 | W4 | W5 |
| Formulation | F1 | F2 | F2 | F3 | F4 |
| Detergent | Dash 2in1 | Dash 2in1 | Ariel liquid | Dash 2in1 | Ariel liquid |

-continued

| | W1 | W2 | W3 | W4 | W5 |
|---|---|---|---|---|---|
| Points | +1.68 | +1.77 | +1.80 | 1.30 | 1.45 |
| Testers | 4 | 4 | 4 | 4 | 4 |

What is claimed is:

1. A formulation comprising:
   a) at least one nitrogen-free polysiloxane compound having a viscosity of 10,000 to 10,000,000 mPa·S at 25° C.,
   b) at least one polyamino-polysiloxane and/or polyammonium-polysiloxane compound b1) which is selected from polysiloxane compounds which contain at least one unit of the formula (I):

—[Q—V]—   (I)

in which Q is selected from the group consisting of:
   —NR—,
   a saturated or unsaturated diamino-functional heterocycle of the formulae:

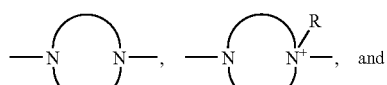, and

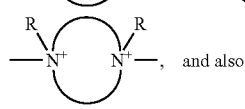 and also an aromatic diamino-functional heterocycle of the formula:

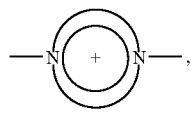, a trivalent radical of the formula:

a trivalent radical of the formula

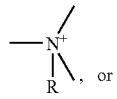, or a tetravalent radical of the formula

in which R in each case is hydrogen or a monovalent organic radical,
   where Q is not bonded to a carbonyl carbon atom,
   V is at least one constituent which is selected from the group consisting of $V^1$, $V^2$ and $V^3$, where
   $V^2$ is selected from divalent or trivalent, straight-chain, cyclic or branched, saturated, unsaturated or aromatic hydrocarbon radicals having up to 1000 carbon atoms (not counting the carbon atoms of the polysiloxane radical $Z^2$ defined below) and may optionally contain one or more groups selected from
   —O—, —CONH—,
   —CONR$^2$—, in which R$^2$ is hydrogen, a monovalent, straight-chain, cyclic or branched, saturated, unsaturated or aromatic hydrocarbon radical having up to 100 carbon atoms, may contain one or more groups selected from —O—, —NH—, —C(O)— and —C(S)—, and may optionally be substituted by one or more substituents selected from the group consisting of a hydroxyl group, an optionally substituted heterocyclic group preferably containing one or more nitrogen atoms, amino, alkylamino, dialkylamino, ammonium, polyether radicals and polyether ester radicals, where, when a plurality of —CONR$^2$— groups is present, they may be the same or different, —C(O)— and —C(S)—, and
   the radical $V^2$ may optionally be substituted by one or more hydroxyl groups, and
   the radical $V^2$ contains at least one group —$Z^2$— of the formula

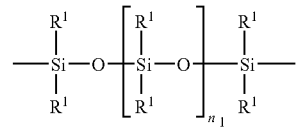

in which
   $R^1$ may be the same or different and is selected from the group consisting of: $C_1$ to $C_{22}$ alkyl, fluoro($C_1$-$C_{10}$) alkyl and $C_6$-$C_{10}$ aryl, and
   $n_1$=20 to 1000,
   $V^1$ is selected from divalent, straight-chain, cyclic or branched, saturated, unsaturated or aromatic hydrocarbon radicals which have up to 1000 carbon atoms and may optionally contain one or more groups selected from
   —O—, —CONH—,
   —CONR$^2$—, in which R$^2$ is as defined above, where the R$^2$ groups in the $V^1$ and $V^2$ groups may be the same or different,
   —C(O)—, —C(S)— and —$Z^1$—, where —$Z^1$— is a group of the formula

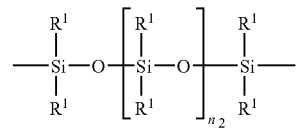

in which
   $R^1$ is as defined above, where the $R^1$ groups in the groups $V^1$ and $V^2$ groups may be the same or different, and
   $n_2$=0 to 19,
   and the radical $V^1$ may if desired be substituted by one or more hydroxyl groups,
   $V^3$ is a trivalent or higher-valency, straight-chain, cyclic or branched, saturated, unsaturated or aromatic hydrocarbon radical which has up to 1000 carbon atoms, may optionally contain one or more groups selected from
   —O—, —CONH—, —CONR$^2$—, in which R$^2$ is as defined above, —C(O)—, —C(S)—, —$Z^1$— which is as defined above, —$Z^2$— which is as defined above and $Z^3$, where $Z^3$ is a trivalent or higher-valency organopolysiloxane unit, and may optionally be substituted by one or more hydroxyl groups, where, in said polysiloxane compound, in each case one or more $V^1$ groups, one or more $V^2$ groups and/or one or more $V^3$ groups may be present, with the provisos (i) that said polysiloxane compound contains a plurality of $V^2$ groups, and (ii) that the tri- and tetravalent Q radicals either serve to branch the main chain formed from Q and V, so that the valencies which do not serve for bonding in the main chain bear further branches formed from —[Q—V]— units, or the tri- and tetravalent Q radicals are saturated with $V^3$ radicals within a linear main chain without formation of a branch, and wherein the positive charges resulting from ammonium groups are neutralized by organic or inorganic acid anions, and acid addition salts thereof, and optionally at least one amino-polysiloxane and/or ammonium-polysiloxane compound b2), c) one or more silicone-free surfactants selected from the group consisting of nonpolymerized organic quaternary ammonium compounds, d) optionally one or more coacervate phase formation agents, and e) optionally one or more carrier substances selected from the group consisting of solid carrier substances f), liquid carrier substances g), and combinations thereof.

2. The formulation as claimed in claim 1, characterized in that it contains, based on the total amount of components a) and b), from 5 to 99% by weight of component a) and
from 1 to 95% by weight of component b).

3. The formulation as claimed in claim 1, characterized in that it contains, based on 100 parts by weight of components a) and b), from 0 to 1500 parts by weight of components c), d) and e).

4. The formulation as claimed in claim 1, characterized in that it contains, based on 100 parts by weight of components a) and b), from 0 to 70 parts by weight of component c).

5. The formulation as claimed in claim 1, characterized in that it contains, based on 100 parts by weight of components a) and b), from 0 to 10 parts by weight of component d).

6. The formulation as claimed in claim 1, characterized in that it contains, based on 100 parts by weight of components a) and b), from 0 to 710 parts by weight of component f).

7. The formulation as claimed in claim 1, characterized in that it contains, based on 100 parts by weight of components a) and b), from 0 to 710 parts by weight of component g).

8. The formulation as claimed in claim 1, characterized in that component a) is at least one constituent which is selected from the group consisting of: straight-chain, cyclic, branched and partially crosslinked polyorganosiloxanes.

9. The formulation as claimed in claim 1, characterized in that the amino- and/or ammonium-polysiloxane compound b2) is a polysiloxane compound which contains amino and/or ammonium groups in the pendent groups of a polyorganosiloxane main chain.

10. The formulation as claimed in claim 1, characterized in that the coacervate phase formation agent as component d) comprises at least one constituent which is selected from cationic, silicone-free polymer compounds.

11. The formulation as claimed in claim 1, characterized in that a solid carrier substance f) is present, and in that the solid carrier substance f) is at least one constituent which is selected from the group of the water-soluble compounds which have a solubility in water of at least 100 grams/liter at 20° C.

12. The formulation as claimed in claim 1, characterized in that a liquid carrier substance g) is present, and in that the liquid carrier substance g) is at least one constituent which is selected from the group consisting of water and water-miscible organic solvents.

13. The formulation as claimed in claim 1, characterized in that it is solid or liquid at 40° C.

14. A process for preparing the formulation as claimed in claim 1, which comprises the steps of:

a) mixing components a) and b) to give a homogeneous premixture, and b) optionally introducing components c), d) and/or e).

15. A method of applying a cosmetic comprising applying the formulation as claimed in claim 1.

16. A method of treating fibers or finishing fibers comprising applying the formulation as claimed in claim 1 to fibers.

17. A method of treating textiles, fiberlike materials, or paper, comprising applying the formulation as claimed in claim 1 to textiles, fiberlike, or paper.

18. A method of softening a textile comprising applying the formulation as claimed in claim 1 to a textile.

19. A method of cleaning laundry comprising applying to laundry the formulation as claimed in claim 1.

20. A method of surface treating a substrate comprising applying to a substrate the formulation as claimed in claim 1.

* * * * *